(12) United States Patent
Krebs et al.

(10) Patent No.: US 8,449,583 B2
(45) Date of Patent: May 28, 2013

(54) FASTENER ASSEMBLY

(75) Inventors: Viktor E. Krebs, Rocky River, OH (US); Wael K. Barsoum, Bay Village, OH (US); Jonathan H. Krapf, Rocky River, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 729 days.

(21) Appl. No.: 12/613,792

(22) Filed: Nov. 6, 2009

(65) Prior Publication Data
US 2010/0198276 A1 Aug. 5, 2010

Related U.S. Application Data

(63) Continuation-in-part of application No. 11/865,094, filed on Oct. 1, 2007, now Pat. No. 7,857,840.

(60) Provisional application No. 60/848,822, filed on Oct. 2, 2006.

(51) Int. Cl.
*A61B 17/84* (2006.01)
(52) U.S. Cl.
USPC ............... 606/300; 606/62; 606/63; 606/64; 606/327; 411/32; 411/45
(58) Field of Classification Search
USPC 606/63–68, 310, 313, 318, 326, 327; 411/32, 411/33, 45–48, 344
See application file for complete search history.

(56) References Cited

U.S. PATENT DOCUMENTS

| | | |
|---|---|---|
| 1,278,025 A | 9/1918 | Salmons |
| 1,700,354 A | 1/1929 | Foss |
| 2,381,050 A | 8/1945 | Hardinge |
| 2,438,533 A | 3/1948 | Booth |
| 2,490,364 A | 12/1949 | Livingston |
| 2,699,774 A | 1/1955 | Livingston |
| 3,044,340 A | 7/1962 | Luhm |
| 3,198,058 A | 8/1965 | Barry |

(Continued)

FOREIGN PATENT DOCUMENTS
WO  WO 03/007830 A1  1/2003

OTHER PUBLICATIONS

Cook et al., "Lumbosacral Fixation Using Expandable Pedicle Screws: An Alternative in Reoperation and Osteoporosis", *The Spine Journal 1* (2001) 109-114.

*Primary Examiner* — Nicholas Woodall
(74) *Attorney, Agent, or Firm* — Tarolli, Sundheim, Covell & Tummino LLP

(57) ABSTRACT

An improved fastener apparatus includes an outer sleeve which is moved into a patient's body tissue. A distal end portion of the outer sleeve is expanded in the patient's body tissue. An inner sleeve is moved axially through the outer sleeve and a distal end of the inner sleeve is expanded in the patient's body tissue. The fastener apparatus may be provided with an external thread convolution on either or both of the inner and outer sleeves. During expansion of the distal end portion of either the inner or outer sleeve, a proximal end portion of the outer sleeve may be gripped and pulled to offset forces applied to the distal end portion of one of the sleeves. Although inner and outer sleeves may advantageously be utilized, the fastener apparatus may be constructed with only a single sleeve or three or more sleeves if desired. A secondary fastener assembly may be moved through a main fastener assembly.

16 Claims, 9 Drawing Sheets

U.S. PATENT DOCUMENTS

| | | |
|---|---|---|
| 3,234,842 A | 2/1966 | Sauter |
| 3,846,846 A | 11/1974 | Fischer |
| 4,770,660 A | 9/1988 | Averill |
| 4,806,053 A | 2/1989 | Herb |
| 4,908,035 A | 3/1990 | Deckner et al. |
| 4,955,886 A | 9/1990 | Pawluk |
| 5,290,318 A | 3/1994 | Ling et al. |
| 5,413,603 A | 5/1995 | Noiles et al. |
| 5,489,210 A | 2/1996 | Hanosh |
| 5,533,851 A | 7/1996 | Remmers |
| 5,601,558 A | 2/1997 | Torrie et al. |
| 5,634,750 A | 6/1997 | Frischmann et al. |
| 5,653,709 A | 8/1997 | Frigg |
| 6,010,505 A | 1/2000 | Asche et al. |
| 6,010,535 A | 1/2000 | Shah |
| 6,096,040 A | 8/2000 | Esser |
| 6,228,086 B1 | 5/2001 | Wahl et al. |
| 6,299,642 B1 | 10/2001 | Chan |
| 6,355,042 B2 | 3/2002 | Winquist et al. |
| 6,443,954 B1 * | 9/2002 | Bramlet et al. ............ 606/62 |
| 6,554,833 B2 * | 4/2003 | Levy et al. ............ 606/63 |
| 6,579,290 B1 | 6/2003 | Hardcastle et al. |
| 6,613,053 B1 | 9/2003 | Collins et al. |
| 6,676,346 B1 | 1/2004 | Frischmann et al. |
| 6,712,820 B2 | 3/2004 | Orbay |
| 6,719,509 B1 | 4/2004 | Huang et al. |
| 7,001,388 B2 | 2/2006 | Orbay et al. |
| 7,004,973 B2 | 2/2006 | Zweymuller |
| 2001/0036391 A1 | 11/2001 | Kaibach et al. |
| 2004/0138665 A1 | 7/2004 | Padget et al. |
| 2004/0176767 A1 | 9/2004 | Bickley |
| 2004/0230194 A1 | 11/2004 | Urbanski et al. |
| 2004/0254581 A1 | 12/2004 | Leclair |
| 2005/0123372 A1 | 6/2005 | Sato |
| 2005/0240188 A1 | 10/2005 | Chow et al. |

\* cited by examiner

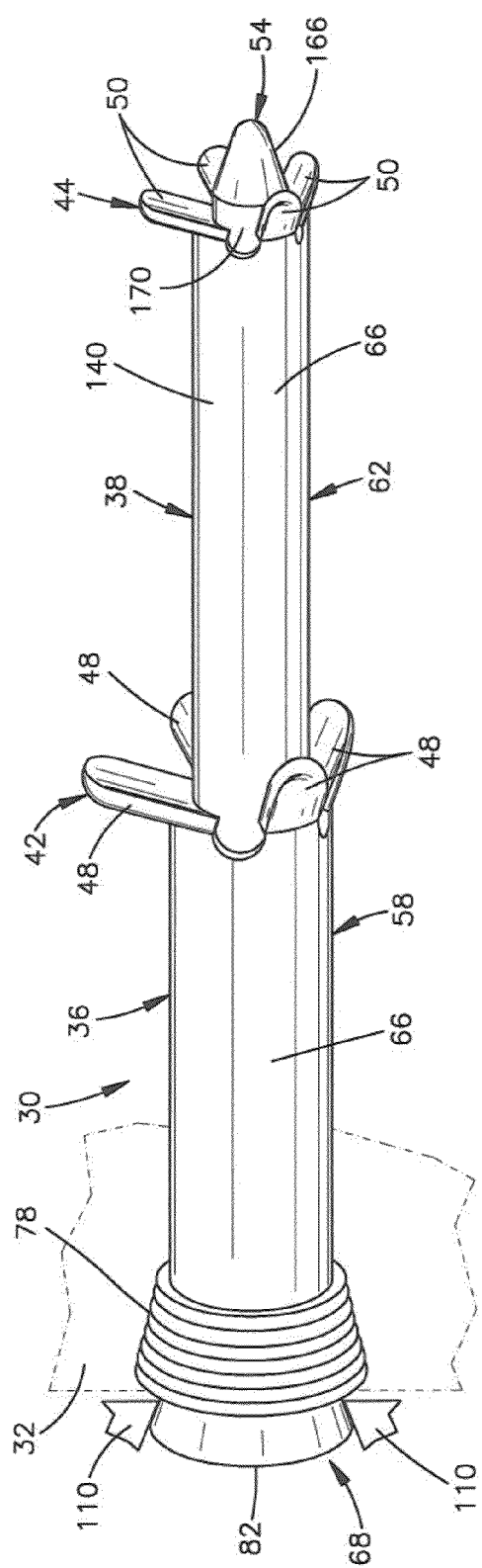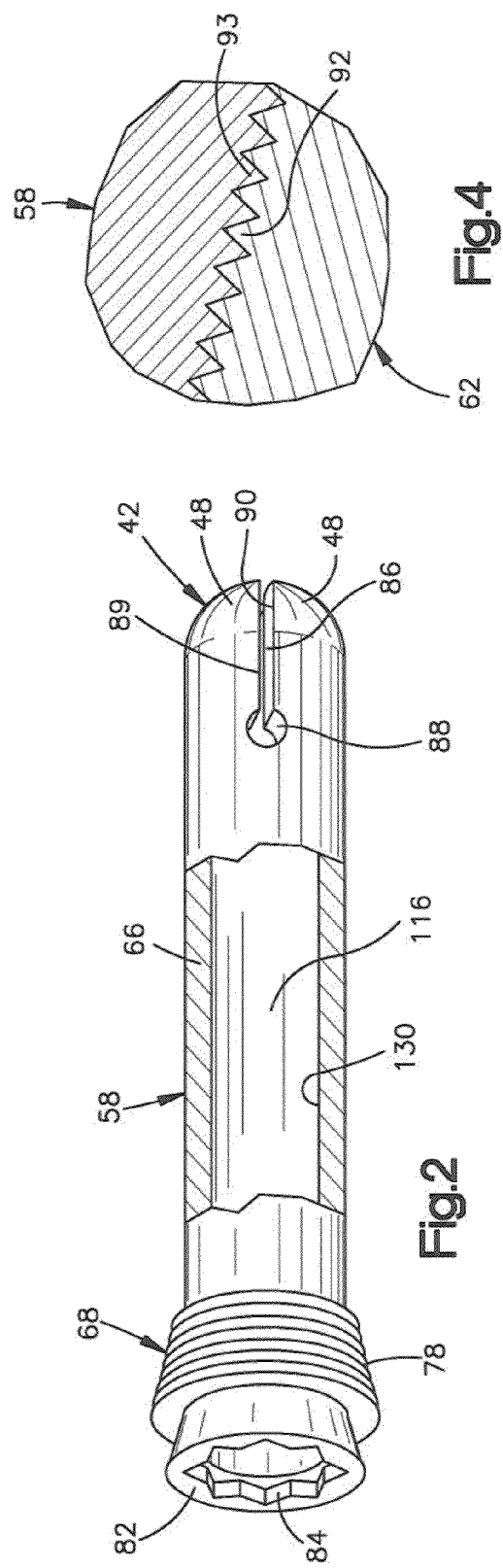

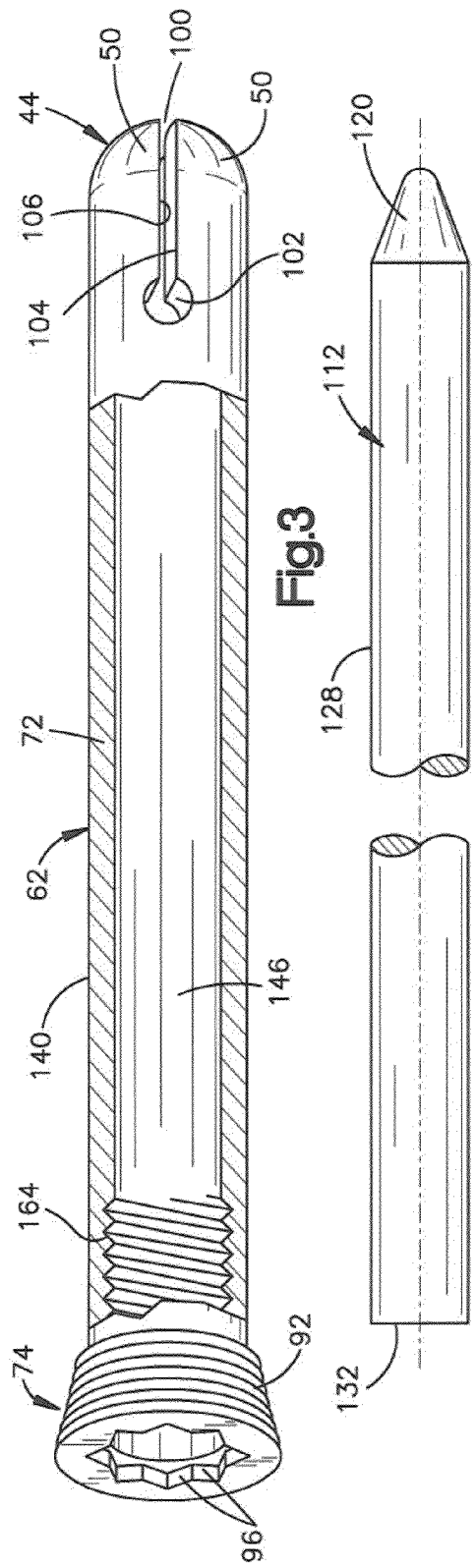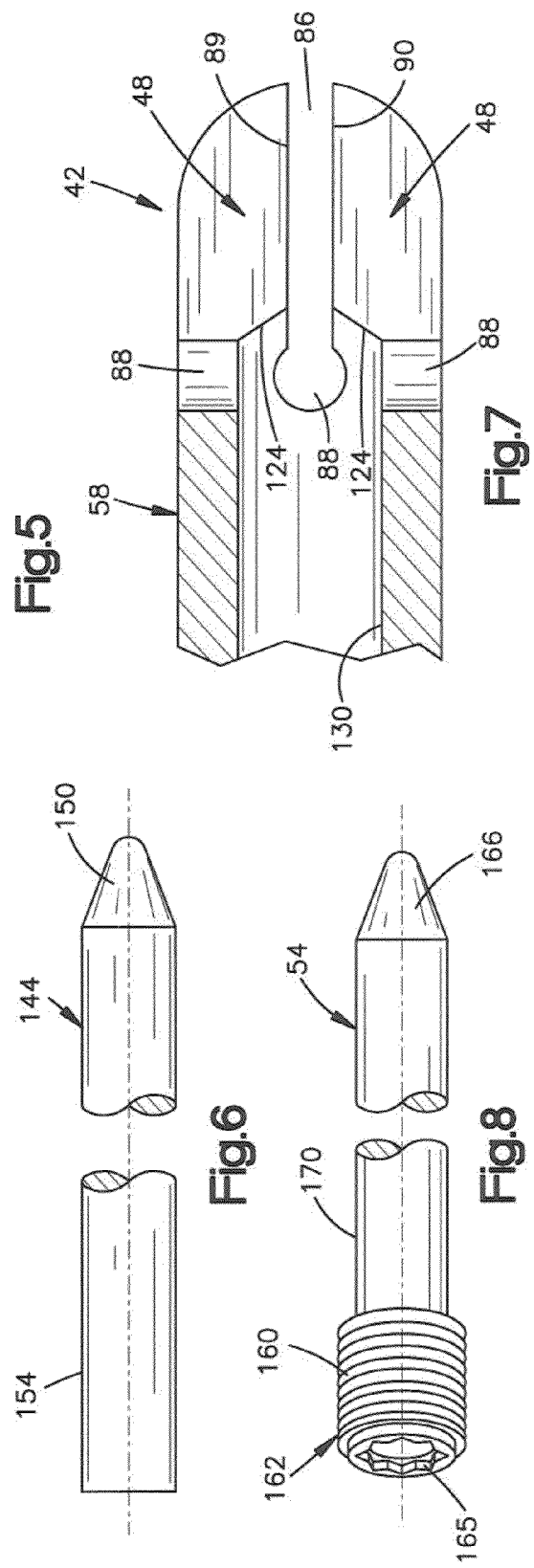
Fig.3
Fig.5
Fig.6
Fig.7
Fig.8

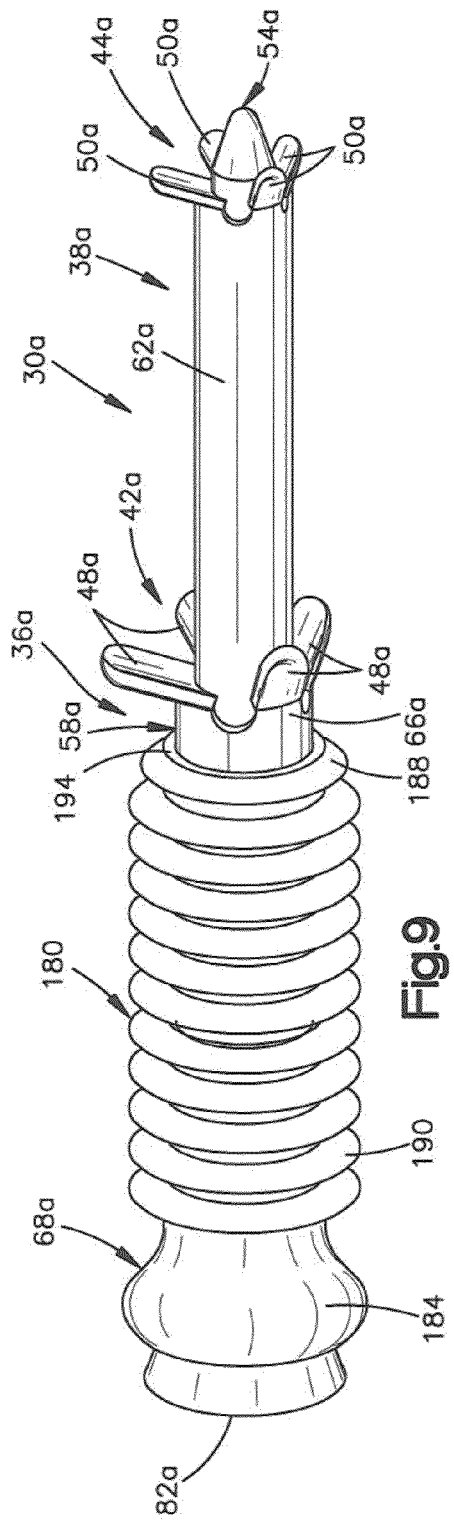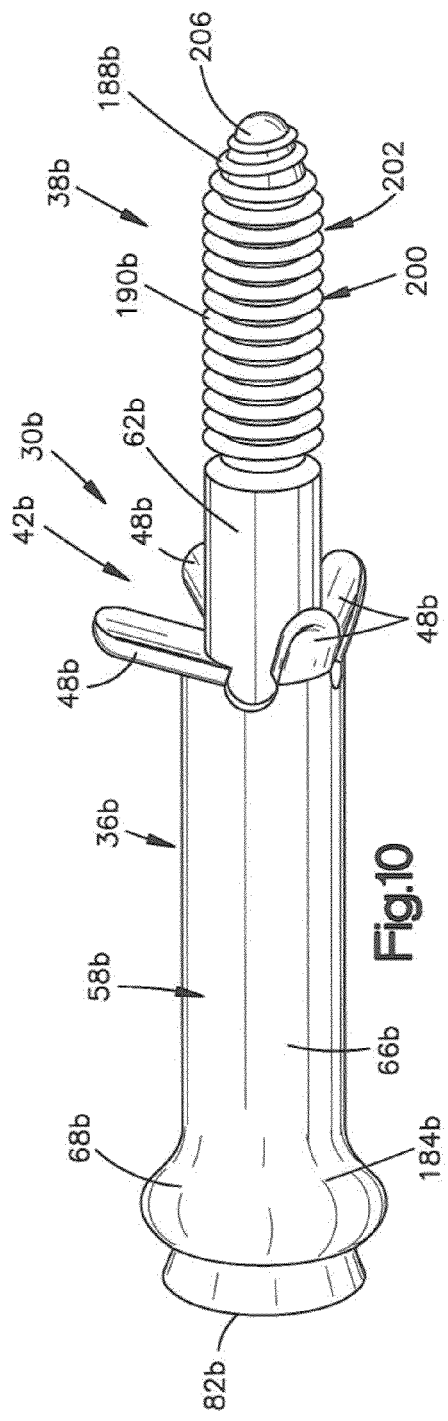

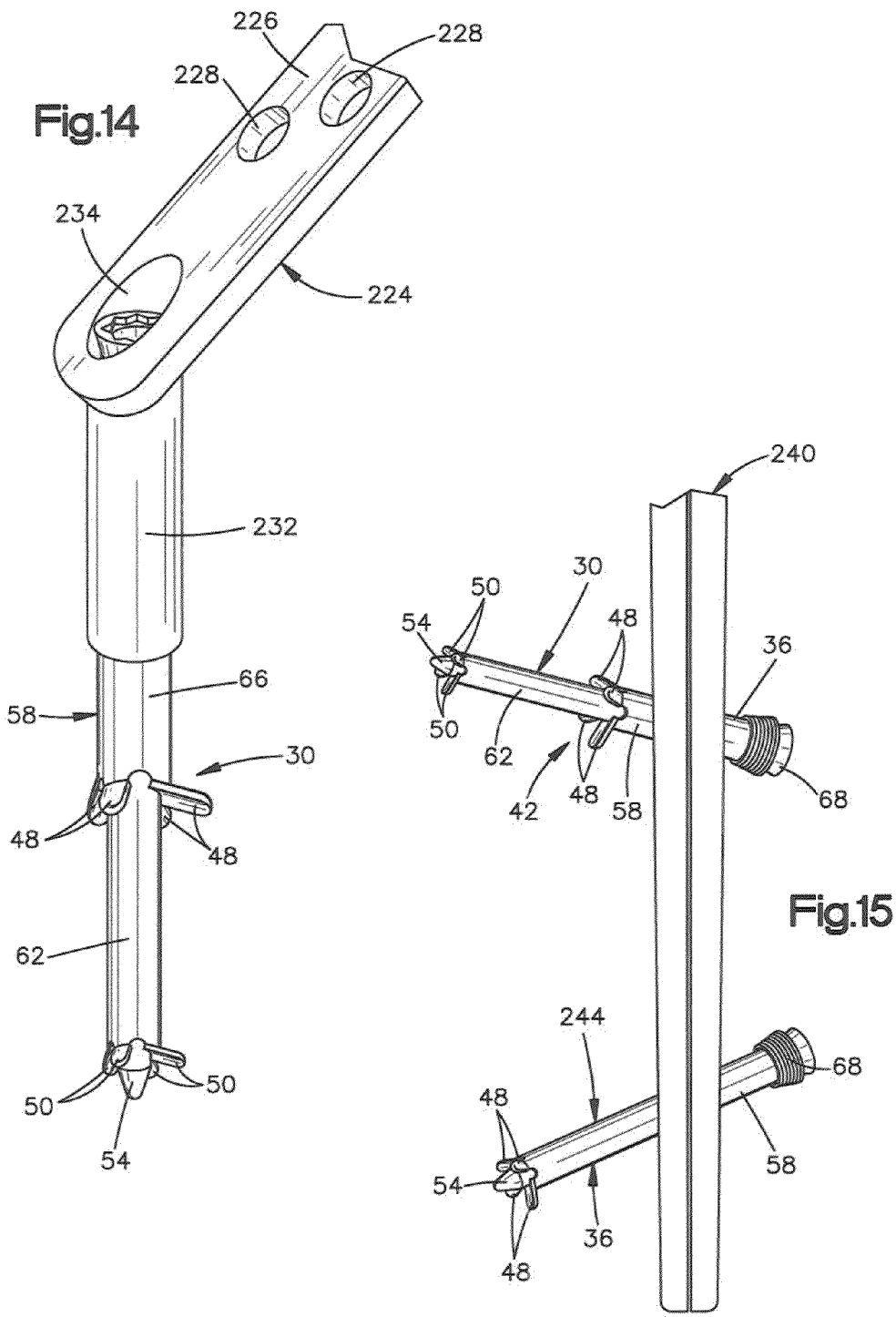

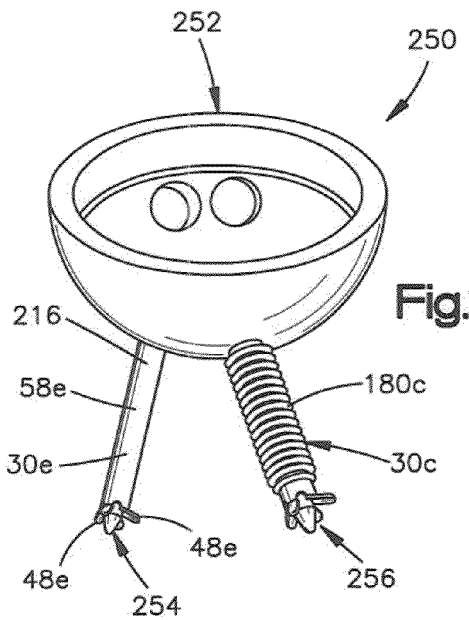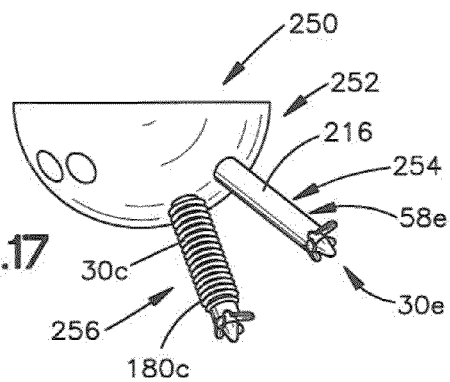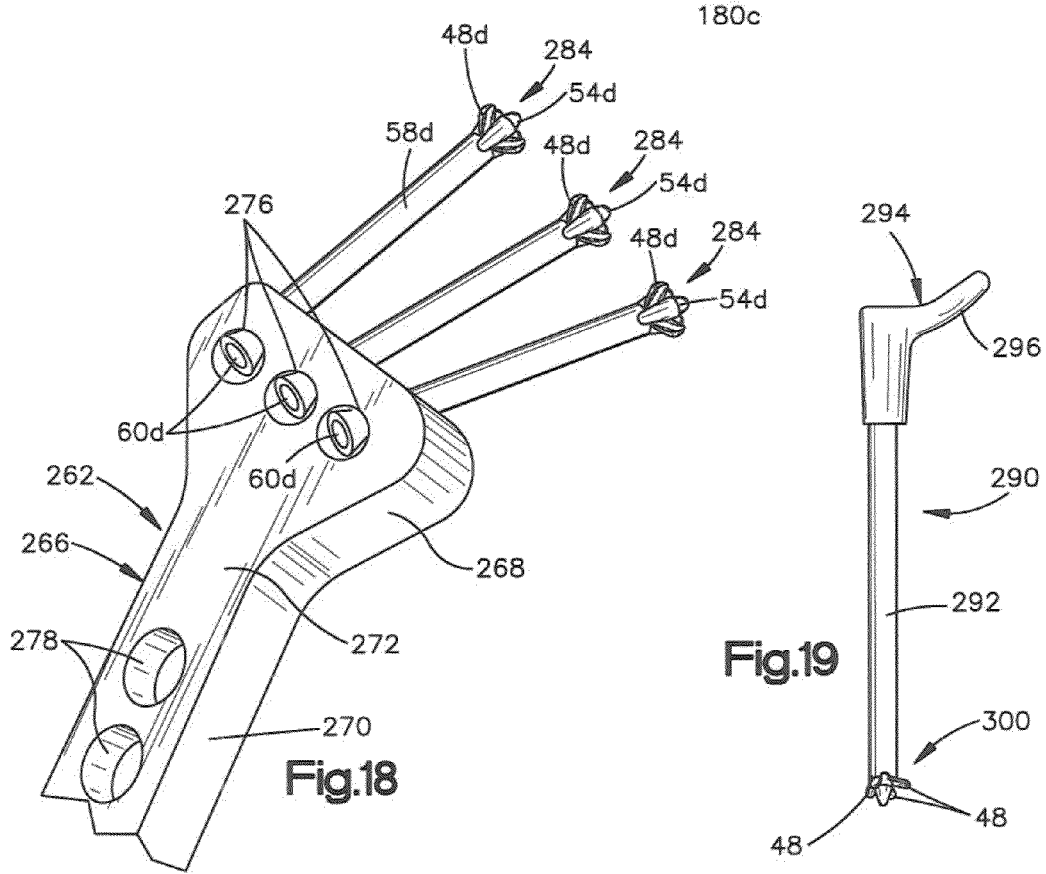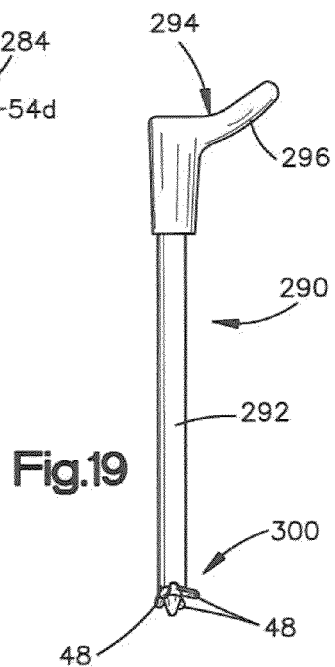

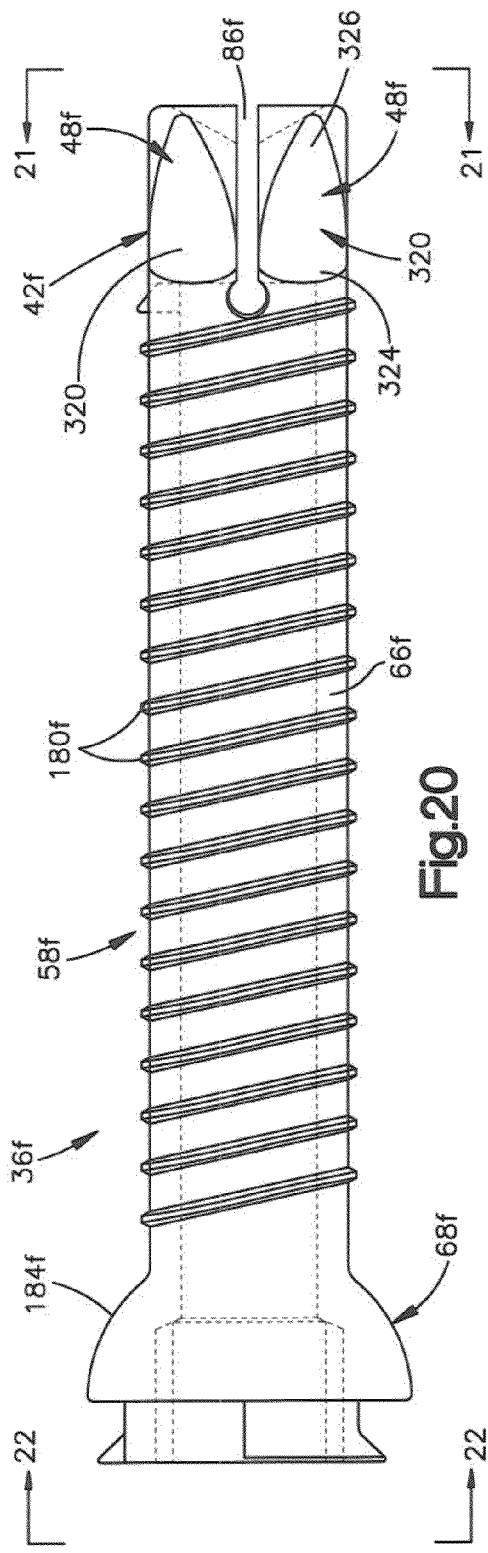
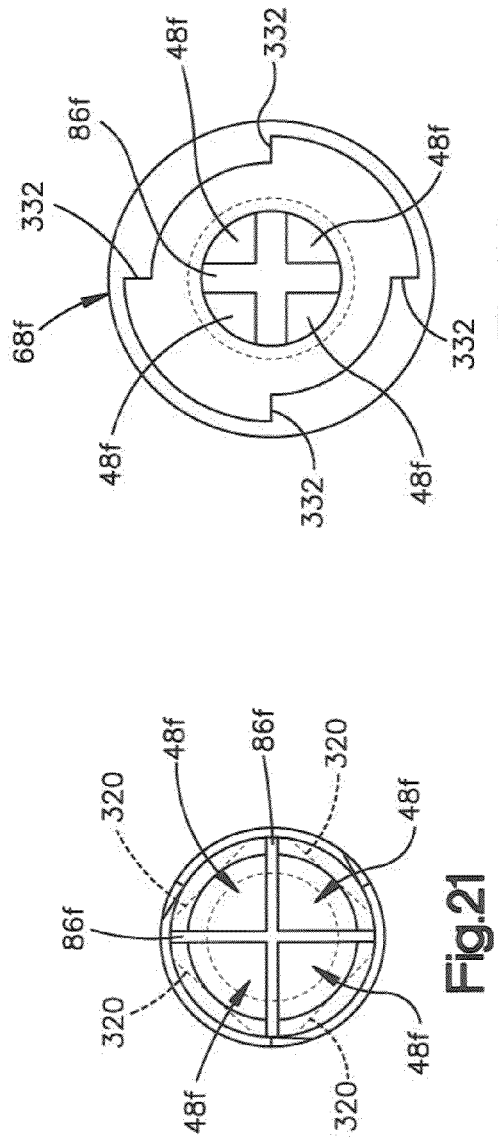

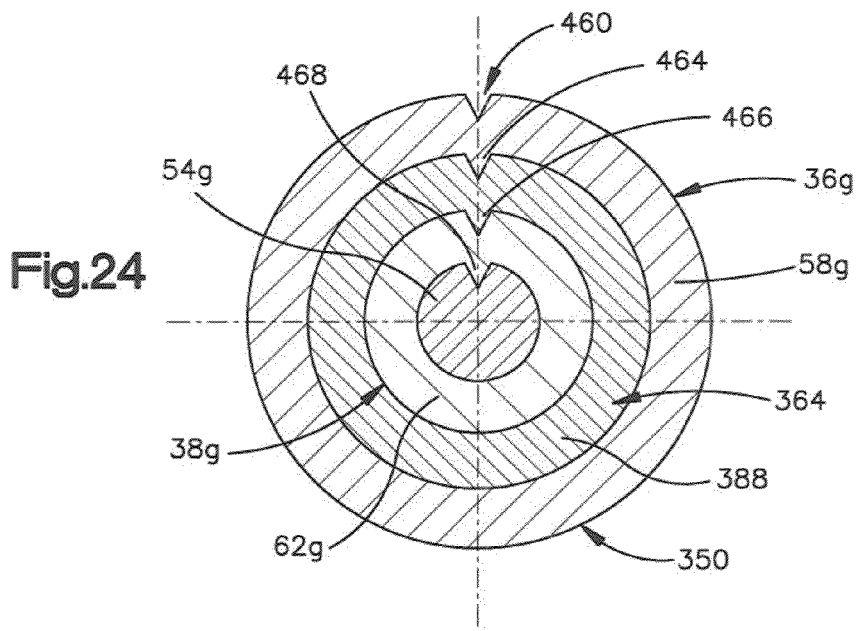
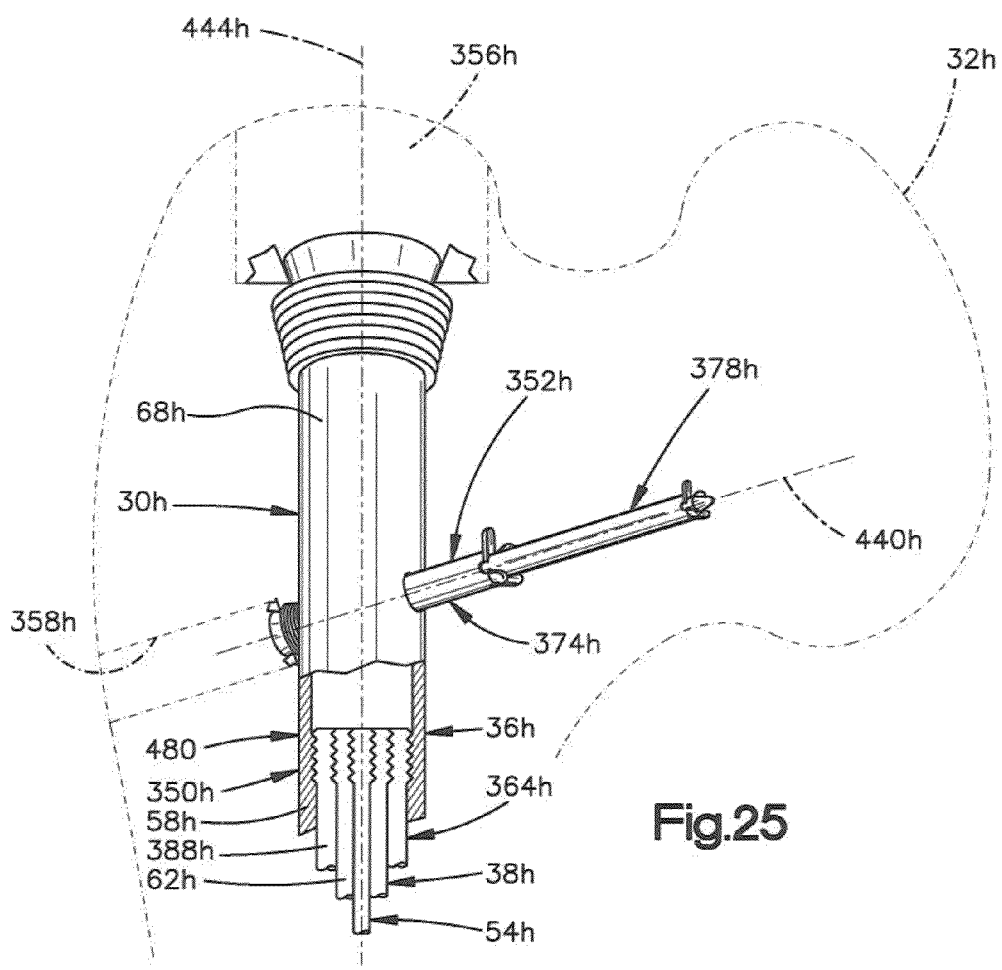

FASTENER ASSEMBLY

RELATED APPLICATIONS

This application IS A CONTINUATION-IN-PART OF U.S. patent application Ser. No. 11/865,094 filed Oct. 1, 2007 now U.S. Pat. No. 7,857,840 and which claims priority to U.S. Provisional Patent Application Ser. No. 60/848,822 Filed Oct. 2, 2006 by Victor E. Krebs, et al. The benefit of the earlier filing dates of the aforementioned applications is hereby claimed. The disclosures in the aforementioned U.S. Provisional Patent Application Ser. No. 60/848,822 and in U.S. patent application Ser. No. 11/865,094 are hereby incorporated herein in their entirety by this reference thereto.

BACKGROUND OF THE INVENTION

The present invention relates to a new and improved fastener apparatus and the manner in which it is utilized in association with a patient's body tissue.

Fasteners have previously been utilized in association with hard and/or soft tissue in a patient's body. The fasteners have been utilized in association with fractures and/or broken bones. The fasteners have been used to secure one portion of a bone to another portion of a bone to facilitate proper healing of a fracture or break in the bone. The fasteners have also been utilized in association with implants, such as a member which spans a portion of a bone.

In addition, fasteners have been utilized to attach or reattach soft tissue to bone. For example, fasteners have been used to attach ligaments to bone. Fasteners have also been utilized to interconnect soft tissue.

SUMMARY OF THE INVENTION

The present invention relates to a new and improved fastener apparatus and a method of utilizing the fastener apparatus in association with a patient's body tissue. A fastener apparatus constructed in accordance with the present invention may be used in anyone of many different ways with body tissue. For example, a fastener apparatus constructed in accordance with the present invention may be used with body tissue in any of the ways previously mentioned herein. Of course, the fastener apparatus may be used with body tissue in ways which have not been previously mentioned herein.

In one embodiment of the method and/or apparatus of the invention, the fastener apparatus includes a fastener assembly having a first sleeve which is moved into a patient's body tissue. A distal end portion of the first sleeve is extended in the patient's body tissue. At least a portion of a second sleeve is moved through the first sleeve. A distal end portion of the second sleeve is extended in the patient's body tissue. During extension of the first sleeve and/or the second sleeve, a proximal end portion of the first sleeve may be gripped and pulled.

In another embodiment of the method and/or apparatus of the invention, a first sleeve is rotated as it is moved into the patient's body tissue. As the first sleeve is rotated, a thread convolution connected with the first sleeve engages the patient's body tissue. At least a portion of a second sleeve is moved axially through the first sleeve. A distal end portion of the second sleeve is extended in the patient's body tissue.

In another embodiment of the method and/or apparatus of the invention, a first sleeve is moved into a patient's body tissue and a distal end portion of the first sleeve is extended. At least a portion of a second sleeve is moved through the first sleeve into the patient's body tissue. As the second sleeve is moved into the patient's body tissue, the second sleeve is rotated about its longitudinal central axis to engage the patient's body tissue with a thread convolution connected with the second sleeve.

In another embodiment of the method and/or apparatus of the invention, a first fastener assembly is moved into a patient's body tissue with a distal end portion leading. A second fastener assembly is moved into the patient's body tissue with a distal end portion leading. The distal end portion of the second fastener assembly is moved through a portion of the first fastener assembly. The distal end portions of the first and/or second fastener assemblies are extended in the patient's body tissue.

A fastener apparatus constructed and/or used in accordance with the present invention may have only a single sleeve which is moved into a patient's body tissue. An actuator member is moved into a central opening in the sleeve and pressed against a distal end portion of the sleeve to expand the sleeve. A proximal end portion of the sleeve is gripped and pulled during pressing of the actuator member against the distal end portion of the sleeve. A retainer member may be moved into the sleeve.

In another embodiment of the invention, a first fastener assembly is moved into the patient's body tissue. A distal end portion of the first fastener assembly is extended at a plurality of locations along a longitudinal axis of the first fastener assembly. A second fastener assembly is moved into the patient's body tissue. The distal end portion of the second fastener assembly is moved through a proximal end portion of the first fastener assembly. The distal end portion of the second fastener assembly is extended in the patient's body tissue.

It should be understood that the method and apparatus of the present invention have a plurality of features. These features may be utilized together in the manner disclosed herein. Alternatively, the features may be utilized separately or in different combinations with each other or in combination with one or more features from the prior art. For example, an embodiment of the apparatus may include only a single sleeve or may include two or more sleeves. As another example, a fastener apparatus constructed in accordance with the present invention may be used in association with an implant having any one of many different constructions.

BRIEF DESCRIPTION OF THE DRAWINGS

The foregoing and other features of the invention will become more apparent upon a consideration of the following description taken in connection with the accompanying drawings wherein:

FIG. 1 is a schematic pictorial illustration of a fastener assembly or apparatus constructed and used in accordance with the present invention;

FIG. 2 is a partially broken away schematic pictorial illustration of an outer sleeve utilized in the fastener apparatus of FIG. 1, the outer sleeve being illustrated in a retracted condition prior to expansion of a distal end portion of the outer sleeve;

FIG. 3 is a partially broken away schematic pictorial illustration of an inner sleeve utilized in the fastener apparatus of FIG. 1, the inner sleeve being illustrated in a retracted condition prior to expansion of a distal end portion of the inner sleeve;

FIG. 4 is a fragmentary schematic sectional view illustrating how an internal thread convolution on the outer sleeve of FIG. 2 engages an external thread convolution on the inner sleeve of FIG. 3;

FIG. 5 is a fragmentary schematic illustration of an actuator member utilized to expand the distal end portion of the outer sleeve of FIG. 2;

FIG. 6 is a fragmentary schematic illustration of an actuator member utilized to expand the distal end portion of the inner sleeve of FIG. 3;

FIG. 7 is an enlarged fragmentary schematic sectional view of a portion of the distal end portion of the outer sleeve of FIG. 2;

FIG. 8 is a fragmentary schematic illustration of a retainer member which is received in the inner sleeve of FIG. 3 to retain the distal end portion of the inner sleeve in the expanded condition illustrated in FIG. 1;

FIG. 9 is a schematic pictorial illustration, similar to FIG. 1, of a fastener assembly or apparatus having an external thread convolution on an outer sleeve;

FIG. 10 is a schematic pictorial illustration, similar to FIGS. 1 and 9, of a fastener assembly or apparatus having an external thread convolution on an inner sleeve;

FIG. 14 is a fragmentary schematic pictorial illustration depicting the manner in which the fastener apparatus of FIGS. 1-13 may be utilized in association with a plate to be implanted in a patient's body;

FIG. 15 is a schematic pictorial illustration depicting the manner in which the fastener apparatus of FIGS. 1-13 may be utilized with a nail to be implanted in a patient's body;

FIG. 16 is a schematic pictorial illustration depicting the manner in which the fastener apparatus of FIGS. 1-13 may be utilized with a socket joint replacement cup to be implanted in a patient's body;

FIG. 17 is a schematic side elevational view of the apparatus of FIG. 16;

FIG. 18 is a fragmentary schematic illustration depicting the manner in which the fastener apparatus of FIGS. 1-13 may be utilized with a plate to be implanted in a patient's body;

FIG. 19 is a schematic illustration depicting the manner in which the fastener apparatus of FIGS. 1-13 may be utilized with an implant for use in joint replacement;

FIG. 20 is a schematic illustration of an outer sleeve of a fastener assembly or apparatus;

FIG. 21 is an end view, taken generally along the line 21-21 of FIG. 20, further illustrating the construction of the outer sleeve;

FIG. 22 is an end view, taken generally along the line 22-22 of FIG. 20, further illustrating the construction of the outer sleeve;

FIG. 24 is a schematic sectional view, taken generally along the line 24-24 of FIG. 23, illustrating index surfaces for positioning sleeves of the main fastener assembly relative to each other; and FIG. 25 is a fragmentary schematic illustration, generally similar to FIG. 23, depicting a fastener assembly having a relatively thick secondary fastener assembly which extends through a main fastener assembly.

DESCRIPTION OF SPECIFIC PREFERRED EMBODIMENTS OF THE INVENTION

General Description

Figure 11:
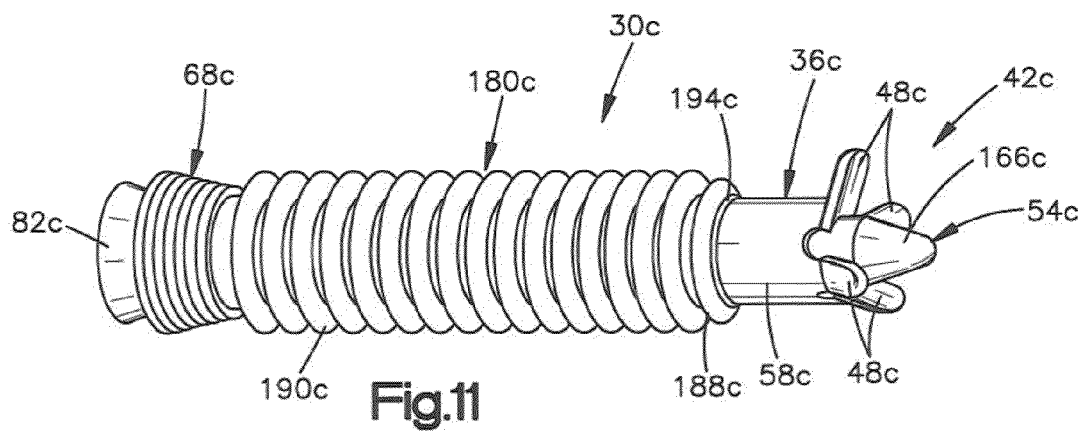
FIG. 11 is a schematic pictorial illustration of a fastener assembly or apparatus having a sleeve with an external thread convolution.

A fastener assembly or apparatus 30 is illustrated schematically in FIG. 1 in association with body tissue 32. The body tissue 32 may be either hard tissue or soft tissue. Alternatively, the fastener assembly or apparatus 30 may be utilized in association with both hard and soft body tissue.

The fastener apparatus 30 includes an outer fastener assembly 36 and an inner fastener assembly 38. The outer and inner fastener assemblies 36 and 38 are disposed in a coaxial relationship and have similar constructions. However, the inner fastener assembly 38 is longer than the outer fastener assembly 36. Although two fastener assemblies 36 and 38 have been illustrated schematically in FIG. 1, a greater or lesser number of fastener assemblies may be utilized if desired.

The fastener apparatus 30 is secured in body tissue 32 by extension of a distal or right (as viewed in FIG. 1) end portion 42 of the outer fastener assembly 36 and extension of a distal or right end portion 44 of the inner fastener assembly 38. The distal end portion 42 of the outer fastener assembly 36 is extended before the distal end portion 44 of the inner fastener assembly 38 is extended. The distal end portion 42 of the outer fastener assembly 36 is extended before or at the same time that the inner fastener assembly 38 is telescopically inserted into the outer fastener assembly.

When the fastener apparatus 30 is in the extended condition of FIG. 1, arm sections 48 on the distal end portion 42 of the outer fastener assembly 36 extend radially outward in a circular array and engage body tissue 32 to hold the fastener apparatus against movement relative to the body tissue. Similarly, when the fastener apparatus 30 is in the extended condition of FIG. 1, arm sections 50 on the distal end portion 44 of the inner fastener assembly 38 extend radially outward in a circular array and engage the body tissue 32 to hold the fastener apparatus against movement relative to the body tissue.

The arm sections 48 on the distal end portion of the outer fastener assembly 36 engage the inner fastener assembly 38 to hold the arm sections 48 in their radially outwardly projecting extended positions illustrated in FIG. 1. A retainer member 54 is disposed in the inner fastener assembly 38 and is engaged by the arm sections 50 on the distal end portion 44 of the inner fastener assembly. Engagement of the arm sections 50 with the retainer member 54 holds the arm sections 50 in their radially outwardly extended positions illustrated in FIG. 1.

Fastener Assemblies

The outer fastener assembly 36 and inner fastener assembly 38 have the same general construction. The outer fastener assembly 36 includes a generally cylindrical outer sleeve 58 (FIG. 2). The inner fastener assembly 38 includes a generally cylindrical inner sleeve 62 (FIG. 3). The outer sleeve 58 extends around and is coaxial with the inner sleeve 62. Together, the outer and inner fastener assemblies 36 and 38 form the fastener apparatus 30.

The outer sleeve 58 (FIG. 2) has a hollow tubular cylindrical central portion 66, a hollow proximal end portion 68, and the distal end portion 42. The outer sleeve 58 is integrally formed as one piece of metal, such as stainless steel or titanium. Of course, if desired, the outer sleeve 58 may be formed of other biocompatible materials.

The inner sleeve 62 (FIG. 3) includes a hollow tubular cylindrical central portion 72. The central portion 72 of the inner sleeve 62 extends between a hollow proximal end portion 74 and the distal end portion 44. The inner sleeve 62 is integrally formed as one piece of metal, such as stainless steel or titanium. Of course, if desired, the inner sleeve 62 may be formed of other biocompatible materials.

The proximal end portion 68 of the outer sleeve 58 (FIG. 2) has a generally conical exterior configuration and tapers radially inward and axially toward the central portion 66 of the outer sleeve. An external thread convolution 78 is formed as a spiral on the outside of the proximal end portion 68. The external thread convolution 78 is formed as a portion of a cone and has a central axis coincident with a central axis of the outer sleeve 58. The external thread convolution 78 has a circular cross sectional configuration as viewed in a plane extending perpendicular to a central axis of the outer sleeve 58. The external thread convolution 78 may be configured to matingly engage a corresponding thread convolution in an article to be implanted in a patient's body. If desired, the external thread convolution 78 may be configured to engage either hard or soft tissue in a patient's body.

The axially tapered conical configuration of the proximal end portion 68 of the outer sleeve 58 (FIG. 2) enables it to be inserted into a similarly axially tapered conical opening in an implant, such as a bone plate. The outer sleeve is then rotated through less than one complete revolution to tightly engage the external spiral thread convolution 78 with an internal spiral thread convolution on the implant. However, the mating thread convolutions on the implant and outer sleeve 58 may be configured so as to require more than one complete revolution to effect tight engagement with a thread on the implant.

The proximal end portion 68 of the outer sleeve 58 includes an outwardly projecting end portion 82. The end portion 82 is formed as a portion of a right circular cone which is coaxial with the outer sleeve 58 and flares radially and axially outward in a direction away from the central portion 66 of the outer sleeve. The projecting end portion 82 is formed with internal wrenching flats 84 which are engageable by a suitable tool to rotate the outer sleeve 58 about its longitudinal central axis.

The distal end portion 42 (FIG. 2) of the outer sleeve 58 includes the arm sections 48. The identical arm sections 48 are formed by a plurality of equal length slots 86 which extend radially outward from the central axis of the outer sleeve 58. In the embodiment of the invention illustrated in FIGS. 1 and 2, there are four arm sections 48 which are formed by two perpendicular slots 86 in the distal end portion 42 of the outer sleeve 58. Of course, a greater or lesser number of arm sections 48 may be provided in the distal end portion 42 of the outer sleeve 58 if desired.

Each of the diametrically extending slots 86 ends in a circular opening 88 which reduces stress concentrations and facilitates bending of the arm sections 48 from the retracted condition illustrated in FIG. 2 to the extended condition illustrated in FIG. 1. Each of the slots 86 has a pair of parallel side surfaces 89 and 90 (FIGS. 2 and 7). The parallel side surfaces 89 and 90 extend between one of the openings 88 and the distal end of the outer sleeve 58.

The inner sleeve 62 (FIG. 3) has the same general construction as the outer sleeve 58. The cylindrical central portion 72 of the inner sleeve 62 extends between the proximal end portion 74 and distal end portion 44 of the inner sleeve. The hollow proximal end portion 74 of the inner sleeve 68 is formed as a portion of a right circular cone which flares radially and axially outward away from the central portion 72 of the inner sleeve 62. An external thread convolution 92 is formed on the outside of the proximal end portion 74 of the inner sleeve 62. The external thread convolution 92 is a spiral and has a circular cross sectional configuration as viewed in a plane extending perpendicular to a longitudinal central axis of the sleeve 62.

When the inner sleeve 62 is telescopically inserted into the outer sleeve 58, in the manner illustrated in FIG. 1, the external thread convolution 92 on the proximal end portion 74 (FIG. 3) of the inner sleeve 62 is engages a correspondingly shaped internal thread convolution 93 (FIG. 4) formed within the hollow proximal end portion 68 (FIG. 2) of the outer sleeve 58. Engagement of the external thread convolution on the inner sleeve 62 (FIG. 3) with the internal thread convolution 93 (FIG. 4) on the outer sleeve 58 holds the inner and outer sleeves 62 and 58 against axial movement relative to each other. To facilitate rotating the inner sleeve 62 relative to the outer sleeve 58, wrenching flats 96 (FIG. 3) are formed in the proximal end portion 74 of the inner sleeve 62.

Upon insertion of the inner sleeve 62 into the extended outer sleeve 58, the external thread convolution 92 engages the mating thread convolution 93 (FIG. 4) on the inside of the proximal end portion 68 of the outer sleeve 58 (FIG. 2). The axially tapered conical configuration of the external thread convolution 92 on the proximal end portion 74 of the inner sleeve 62 (FIG. 3) enables the external thread convolution 92 on the inner sleeve to be inserted into a similarly axially tapered internal thread convolution 93 on the inside of the outer sleeve 58. The inner sleeve 62 is then rotated through less than one complete revolution to tightly engage the external thread convolution 92 on the inner sleeve with a similarly configured internal thread convolution on the outer sleeve 58.

It should be understood that the outer sleeve 58 and inner sleeve 62 may be interconnected in ways other than the thread convolutions 92 and 93 (FIG. 4). For example, one or more locking lugs may be provided on the inner and/or outer sleeves 58 and 62. Alternatively, an interference fit may be provided between the inner and outer sleeves 58 and 62. For example, the interference fit may be provided by having conical surfaces on the outer and inner sleeves 58 and 62 with slightly different apex angles. If desired, a locking clip may be used to interconnect the inner and outer sleeves 58 and 62.

The distal end portion 44 (FIG. 3) of the inner sleeve 62 includes the arm sections 50. A pair of radially extending slots 100 in the distal end portion 44 of the inner sleeve 62 form four arm sections 50. Since there are four arm sections 50, there are two perpendicular slots 100 that extend diametrically across the distal end portion 44 of the inner sleeve 62. Of course, a greater or lesser number of arm sections may be defined by the distal end portion 44 of the inner sleeve 62.

Openings 102 are formed at ends of the slots 100 to minimize stress concentrations and facilitate bending of the arm sections from the retracted condition of FIG. 3 to the extended condition of FIG. 1. The slots 100 have parallel side surfaces 104 and 106. The construction of the distal end portion 44 of the inner sleeve 62 is the same as the construction of the distal end portion 42 of the outer sleeve 58. However, the distal end portion 42 of the outer sleeve 58 is larger than the distal end portion 44 of the inner sleeve 62 since the outer sleeve 58 has a larger diameter than the inner sleeve.

Installation of Fastener Apparatus

When the fastener apparatus 30 is to be installed in the body tissue 32 (FIG. 1), the outer fastener assembly 36 is positioned in the body tissue with the outer sleeve 58 in the retracted condition of FIG. 2. The outer sleeve 58 is then operated to the extended condition of FIG. 1. The inner fastener assembly 38 is then telescopically moved into the extended outer fastener assembly 36 with the inner sleeve 62 in the retracted condition of FIG. 3. The distal end portion 44 of the inner sleeve 62 is then operated to the extended condition of FIG. 1.

The retracted outer sleeve 58 may be connected with an implant before or during movement of the outer sleeve into the body tissue 32. In FIG. 1, the outer fastener assembly 36 is positioned directly in the body tissue 32 without being connected to an implant. When the outer fastener assembly 36 is to be disposed in body tissue 32 without being connected to an implant, the external thread convolution 78 on the proximal end portion 68 of the outer sleeve 58 may be replaced by a series of annular rings or by one or more annular radially extending flanges which engage the body tissue 32. Alternatively, the external thread convolution 78 may be replaced by a smooth outer side surface. This smooth outer side surface may be formed as either a portion of a cone or a sphere.

When the outer sleeve 58 is to be installed in soft body tissue, an opening may be formed in the body tissue. The opening may be formed by either cutting or piercing the body tissue. Alternatively, the distal end portion 42 of the outer sleeve may be pressed against the body tissue 32 to form at least a portion of the opening in the body tissue. When the outer sleeve 58 is to be disposed in hard body tissue 32, such as bone, an opening having a diameter which is slightly less than the diameter of the cylindrical central portion 66 of the outer sleeve 58 may be formed in the bone. The bone is drilled to form the opening into which the outer sleeve 58 is inserted.

The outer sleeve 58 is inserted into the body tissue 32 with the retracted distal end portion 42 (FIG. 2) leading. As the outer sleeve 58 is moved into the body tissue 32, the external thread convolution 78 is moved into engagement with the body tissue. A tool is then utilized to engage the wrenching flats 84 to rotate the outer sleeve relative to the body tissue 32 and cause the external thread convolution 78 to form internal threads in the body tissue. The body tissue 32 may be hard or soft body tissue.

When the outer sleeve 58 has been moved to the desired position relative to the body tissue 32, the distal end portion 42 of the outer sleeve 58 is extended. To extend the distal end portion of the outer sleeve 42, the projecting end portion 82 of the outer sleeve 58 is engaged by a gripper 110 (FIG. 1). While the projecting end portion 82 of the outer sleeve 58 is engaged by the gripper 110, a cylindrical actuator member 112 (FIG. 5) is moved into a cylindrical central opening 116 (FIG. 2) in the outer sleeve 58. The actuator member 112 is telescopically inserted into the outer sleeve 58 with a conical nose end portion 120 of the actuator member leading.

The nose end portion 120 of the actuator member 112 (FIG. 5) moves into engagement with sloping side or cam surfaces 124 (FIG. 7) on the arm sections 48. The cam surfaces 124 are skewed at an obtuse angle of more than 100° relative to each other. The included angle between the cam surfaces 124 in FIG. 7 is 118°.

The nose end portion 120 (FIG. 5) of the actuator member 112 is formed as a portion of a right circular cone having a vertex with an angle of less than 100°. The included angle of the nose end portion 112 is approximately 60°. However, the included angle of the nose end portion may be any desired angle which is less than 100°.

In the embodiment of the outer sleeve 58 illustrated in FIG. 7, the cam surfaces 124 slope forward, that is, toward the right as viewed in FIG. 7. However, the cam surfaces 124 may slope backward, that is, toward the left as viewed in FIG. 7. Alternatively, the cam surface 124 may extend perpendicular to a longitudinal central axis of the outer sleeve 58.

As the actuator member 112 is axially moved into outer sleeve 58, a cylindrical outer side surface 128 on the actuator member 112 slides along a cylindrical inner side surface 130 (FIG. 2) of the central opening 116 in the outer sleeve 58. The nose end portion 120 of the actuator member 112 applies a rightward (as viewed in FIG. 7) force against the cam surfaces 124. At the same time, the gripper 110 is pulling the end portion 84 of the outer sleeve toward the left (as viewed in FIG. 1). By applying oppositely directed forces against opposite ends of the outer sleeve 58 with the actuator member 112 and the gripper 110, the outer sleeve is not displaced axially relative to the body tissue 32 as the outer end portion 42 of the sleeve is extended.

As the outer sleeve 58 is operated from the retracted condition of FIGS. 2 and 7 to the expanded or extended condition of FIG. 1, the tissue 32 is deflected by the arm sections 48. The external arm sections 48 and proximal end portion 68 of the outer sleeve engage the body tissue 32 to block axial movement of the outer sleeve 58 relative to the body tissue. If desired, the proximal end portion 68 of the outer sleeve 58 may be configured to extend radially outward to approximately the same extent as the extended arm sections 48. This would tend to enhance resistance of the expanded outer sleeve to axial movement relative to the body tissue 32.

Once the arm sections 48 of the outer sleeve 58 have been moved to the extended condition of FIG. 1 by the application of force against the distal end portion 42 of the outer sleeve by the actuator member 112 (FIG. 5), the actuator member is withdrawn from the outer sleeve 58. The gripper 110 (FIG. 1) maintains a secure grip on the projecting end portion 82 of the outer sleeve 58 as the actuator member 112 is withdrawn from the outer sleeve. The retracted inner sleeve 62 (FIG. 3) is then telescopically inserted into the extended outer sleeve 58.

As the inner sleeve 62 is inserted into the outer sleeve 58, the leading distal end portion 44 of the inner sleeve 62 moves past the extended arm sections 48 on the outer sleeve 58 and into an engagement with the body tissue 32. The inner sleeve continues to move further into the body tissue 32 to the position illustrated in FIG. 1 while the inner sleeve remains in the contracted condition. As the inner sleeve 62 moves past the extended distal end portion 42 of the outer sleeve 36 (FIG. 1), the retracted leading distal end portion 44 (FIG. 3) displaces the body tissue 32. Of course, if the body tissue 32 is hard body tissue, such as bone, an opening would be formed in the body tissue to receive the inner sleeve 62.

As the inner sleeve 62 moves axially into the outer sleeve 58, the outside of the proximal end portion 74 of the inner sleeve 62 moves into engagement with the inside of the proximal end portion 68 of the outer sleeve 58. The inner sleeve 62 may be then rotated to cause the external thread convolution 92 (FIG. 3) on the inner sleeve to engage the internal thread convolution 93 (FIG. 4) in the proximal end portion 68 of the outer sleeve 58 to interconnect the inner and outer sleeves. If desired, the external thread convolution 92 on the inner sleeve 62 may be omitted and the inner sleeve provided with a smooth arcuate surface which engages a similarly shaped smooth arcuate surface within the proximal end portion 68 of the outer sleeve 58. Thus, the proximal end portion 74 of the inner sleeve 62 may be provided with a convex outer side surface which moves into engagement with a concave surface within the proximal end portion 68 of the outer sleeve 58.

During axial movement of the inner sleeve 62 (FIG. 3) into the outer sleeve 58 (FIG. 2), the gripper 110 (FIG. 1) holds the outer sleeve against axial movement relative to the body tissue 32. The gripper 110 is effective to hold the outer sleeve 58 against both axial and rotational movement relative to the body tissue 32 during rotation and axial movement of the inner sleeve 62 relative to the outer sleeve 58 to tightly interconnect the thread convolutions 92 and 93 (FIG. 4).

When the retracted inner sleeve 62 has been telescopically inserted into the expanded outer sleeve 58 and moved to the desired position relative to the body tissue 32, the cam surfaces 124 (FIG. 7) on the arm sections 48 in the distal end portion 42 of the outer sleeve 58 engage a cylindrical outer side surface 140 on the central portion 66 of the inner sleeve 62. Engagement of the arm sections 48 with the outer side surface 140 of the inner sleeve 62 holds the arm sections 48 in the expanded condition illustrated in FIG. 1. Thus, the inner sleeve 62 locks the arm sections 48 in the extended or expanded condition.

Rather than using the actuator member 112 to extend the retracted distal end portion 42 of the outer sleeve 58, the retracted inner sleeve 62 may be utilized to extend the outer sleeve 58. When this is to be done, the retracted inner sleeve 62 is telescopically inserted into the retracted outer sleeve 58. While the gripper 110 pulls on the proximal end portion 68 of the outer sleeve 58, the retracted distal end portion 44 of the inner sleeve is pressed against the cam surfaces 124 on the arm sections 48 of the outer sleeve. The force applied against the cam surfaces 124 by the retracted inner sleeve 62 pivots the arm sections 48 radially outward and moves the body tissue 32.

Once the contracted inner sleeve 62 has been positioned relative to the outer sleeve 58 and body tissue 32, the inner sleeve 62 is operated from the retracted condition of FIG. 3 to the extended condition of FIG. 1. To operate the inner sleeve to the extended condition, a cylindrical actuator member 144 (FIG. 6) is telescopically inserted into a cylindrical central opening 146 (FIG. 3) in the inner sleeve 62. Insertion of the actuator member 144 into the inner sleeve 62 results in a conical nose end portion 150 (FIG. 6) on the actuator member moving into engagement with cam surfaces on the arm sections 50 (FIG. 3) at the distal end portion 44 of the retracted inner sleeve.

The distal end portion 44 of the inner sleeve 62 has the same construction as the distal end portion 42 of the outer sleeve 36. Thus, the arm sections 50 at the distal end portion 44 of the inner sleeve 62 have cam surfaces, corresponding to the cam surfaces 124 (FIG. 7) on the distal end portion 42 of the outer sleeve 58. The cam surfaces on the arm sections 50 at the distal end portion 44 of the inner sleeve 62 have an included angle of more than 100°. Specifically, the included angle is approximately 118°, the same as the cam surfaces 124 on the arm sections 48 at the distal end portion 42 of the outer sleeve 58. The nose end portion 150 (FIG. 6) of the actuator member 144 has a generally conical configuration with a vertex angle of less than 100°. Specifically, the nose end portion 150 has a vertex angle of approximately 60°.

Once the actuator member 144 has engaged the cam surfaces on the arm sections 50 at the distal end portion of the inner sleeve 62, force is applied against a proximal end portion 154 (FIG. 6) of the actuator member 144. At the same time, the gripper 110 (FIG. 1) engages the projecting end portion 82 on the proximal end portion 68 of the outer sleeve 58. The gripper 110 pulls the outer sleeve 58 toward the left (as viewed in FIG. 1) while the actuator member 144 presses toward the right against the distal end portion 44 of the inner sleeve 62.

The force applied against the proximal end portion 154 of the actuator member 144 (FIG. 6) is directed toward the right (as viewed in FIGS. 3 and 6). This force is applied to the cam surfaces on the arm sections 50 of the inner sleeve 62 (FIG. 3). The force is transmitted from distal end portion 44 of the inner sleeve 62 to the thread convolutions 92 and 93 (FIG. 4) interconnecting the proximal end portions 74 and 68 (FIGS. 3 and 2) of the inner sleeve 62 and outer sleeve 58. The gripper 110 holds the proximal end portion 68 of the outer sleeve 58 against movement relative to the body tissue 32.

The force applied to the actuator member 144 to expand the inner sleeve 62 is in an opposite direction to the force applied to the gripper 110. Therefore, the two forces tend to cancel each other. The force which is applied to the inner sleeve 62 firmly presses the outer side of the proximal end portion 74 of the inner sleeve against an inner side of the proximal end portion 68 of the outer sleeve 58.

The force applied against the distal end portion 74 (FIG. 3) of the inner sleeve 62 by the actuator member 144 cams the arm sections 50 radially outward, relative to the inner sleeve, from the retracted condition illustrated in FIG. 3 to the expanded condition illustrated in FIG. 1. As this occurs, body tissue 32 is forced toward the proximal end portions 68 and 74 of the inner and outer sleeves by the arm sections 50. The force transmitted from the gripper 110 (FIG. 1) to the outer sleeve 58 holds both the outer sleeve and the inner sleeve 62 against axial movement relative to the body tissue 32 as the inner sleeve is expanded.

When the arm sections 50 have been moved to their fully expanded or extended conditions in FIG. 1, the actuator member 144 (FIG. 6) is withdrawn from the central opening 146 (FIG. 3) in the inner sleeve 62. Once the actuator member 144 has been withdrawn from the inner sleeve 62, the retainer member 54 (FIG. 8) is moved into the inner sleeve 62 to a location where an external thread convolution 160 (FIG. 8) on a proximal end portion 162 of the retainer member 54 engages an internal thread convolution 164 (FIG. 3) on the inner sleeve 54. A suitable tool engages wrenching flats 165 formed in the proximal end portion 162 of the retainer member 54. The tool rotates the retainer member 54 to tightly engage the thread convolution 160 on the retainer member 54 with the thread convolution 164 on the inner sleeve 62. The inner sleeve 62 and outer sleeve 58 are held against rotation relative to the body tissue by the gripper 110 (FIG. 1) as the retainer member 54 (FIG. 8) is rotated relative to the inner sleeve 62.

A nose end portion 166 on the retainer member 54 extends outward past the cam surfaces on the arm sections 50 and the distal end portion 44 (FIG. 1) of the inner sleeve 62. The arm sections 50 on the distal end portion 44 of the inner sleeve 62 engage a cylindrical outer side surface 170 on the retainer member 54 (FIG. 8). This results in the arm sections 50 being held in the extended condition of FIG. 1 by engagement with the retainer member 54.

External Thread Convolution—Outer Fastener Assembly

In the embodiment of the invention illustrated in FIG. 1, the fastener apparatus 30 is held against axial movement relative to the body tissue 32 by engagement of arm sections 48 and 50 on the outer and inner fastener assemblies 36 and 38 with the body tissue and by engagement of the proximal end portion 68 of the outer sleeve 58 with the body tissue. In the embodiment of the invention illustrated in FIG. 9, an external thread convolution is provided in association with the central portion of the outer sleeve of the fastener apparatus. Since the embodiment of the invention illustrated in FIG. 9 is generally similar to the embodiment of the invention illustrated in FIGS. 1-8, similar numerals will be utilized to designate similar components, the suffix letter "a" to be added to the numerals of FIG. 9 in order to avoid confusion.

A fastener assembly or apparatus 30a includes an outer fastener assembly 36a and an inner fastener assembly 38a. The outer fastener assembly 36a includes a distal end portion 42a and a proximal end portion 68a. The proximal end portion 68a includes a smooth convex arcuate surface 184 having a bulbous configuration. The proximal end portion 68a of the outer fastener assembly 36a is free of a thread convolution at a location corresponding to the location of the external thread convolution 78 on the proximal end portion 68 of the outer sleeve 58 (FIGS. 1 and 2). However, a thread convolution corresponding to the thread convolution 78 (FIG. 2) may be provided on the proximal end portion 68a (FIG. 9) if desired.

A central portion 66a (FIG. 9) of an outer sleeve 58a of the outer fastener assembly 36a is provided with a helical external thread convolution 180. The external thread convolution 180 may be formed of the same biocompatible material as the outer sleeve 58a or of a different material. The illustrated external thread convolution 180 is formed of the same biocompatible metal as the outer sleeve 58a, that is, stainless steel or titanium. However, the external thread convolution 180 may be formed of a different material than the outer sleeve 58a. For example, the outer sleeve 58a may be formed of stainless steel and the external thread convolution 180 formed of a biocompatible polymeric material.

The external thread convolution 180 has a relatively large depth, that is, there is a substantial distance between the crest of the external thread convolution 180 and the root of the external thread convolution. By providing the helical external thread convolution 180 with a relatively large depth, the thread convolution can securely grip body tissue to which the fastener apparatus 30a is connected. The external thread convolution 180 has a crest diameter which is approximately the same as the maximum outside diameter of the proximal end portion 68a. However, the external thread convolution may have a crest diameter which is either larger or smaller than the maximum outside diameter of the proximal end portion 68a.

The external thread convolution 180 is of the self tapping type. To facilitate the formation of an internal thread convolution in either hard or soft body tissue, the self tapping external thread convolution 180 may have a sharply defined crest portion. Alternatively, the self tapping external thread convolution may be configured to form an internal thread convolution with a cam action rather than a cutting action. Although the external thread convolution 180 is a single start thread convolution, the external thread convolution 180 may be a multiple start thread convolution if desired.

When the fastener apparatus 30a is to be utilized in association with bone or hard body tissue, the proximal end portion 68a of the fastener assembly may engage cortical bone while the external thread convolution 180 engages cancellous bone. Alternatively, both the proximal end portion 68a and the external thread convolution 180 may engage cancellous bone. If desired, the smooth convex surface 184 on the proximal end portion 68a of the outer sleeve 58a may engage a corresponding configured concave surface on a bone plate or other implant.

When the fastener apparatus 30a is to be utilized in association with soft body tissue or a combination of soft and hard body tissue, the proximal end portion 68 a may engage either hard body tissue or soft body tissue. If the proximal end portion 68a is to engage soft body tissue, the extent to which the proximal end portion flares radially outward from the central portion 66a may be increased. If desired, a radially extending flange may be provided on the proximal end portion 68a to increase the extent of engagement with soft tissue. As was previously mentioned, an external thread convolution may be provided on the proximal end portion 68a.

When the fastener apparatus 30a is used in association with soft body tissue, the relatively large depth of the external thread convolution 180 enables the external thread convolution to securely connect the fastener assembly with the soft tissue. The proximal end portion 68a may engage either soft tissue or an implant. Alternatively, the proximal end portion 68a may engage hard body tissue, such as bone, while at least a portion of the thread convolution 180 engages soft body tissue.

The thread convolution 180 has a uniform root diameter throughout the extent of the thread convolution. The thread convolution 180 has a tapered leading or distal end portion 188 which is formed as a continuation of a main portion 190 of the thread convolution. The main portion 190 of the thread convolution 180 has a uniform crest diameter to maximize engagement with body tissue. The axially tapered leading end portion 188 of the thread convolution 180 has a crest diameter which decreases in a direction toward the distal end portion 42a of the outer sleeve 58a. The axially tapered crest diameter on the leading end portion 188 of the thread convolution 180 facilitates engagement of the thread convolution with body tissue.

The thread convolution 180 is disposed on a cylindrical tube 194 which is connected to the outer sleeve 58a. The thread convolution 180 and tube 194 are fixedly mounted on the central portion 66a of the outer sleeve 58a when the arm sections 48a are in a retracted condition, corresponding to the retracted condition of the arm sections 48 in FIG. 2. If desired, the tube 194 (FIG. 9) may be omitted and the external thread convolution 180 mounted directly on the central portion 66a of the outer sleeve 58a. Alternatively, the thread convolution 180 may be integrally formed as one piece with the outer sleeve 58a.

The tube 194 may be formed of the same material as the outer sleeve 58a. Alternatively, the tube 194 may be formed of a different material than the outer sleeve. The illustrated tube 194, external thread convolution 180, and outer sleeve 58a are all formed of a biocompatible metal, such as stainless steel or titanium. However, one or more of these components may be formed of a different material or materials if desired. For example, the thread convolution 180 may be formed of a polymeric material and the tube 190 formed of either a polymeric material or metal.

When the fastener assembly or apparatus 30a (FIG. 9) is to be installed in body tissue, similar to the body tissue 32 of FIG. 1, an opening is formed in the body tissue. When the body tissue 32 is hard (bone), a hole having a diameter which is about the same as a root diameter of the external thread convolution 180 may be drilled in the bone. When the body tissue 32 is soft body tissue, an opening may be cut in the body tissue.

With the outer sleeve 58a in a retracted condition, corresponding to the retracted condition of the outer sleeve 58 in FIG. 2, the distal end portion 42a of the outer sleeve 58a is moved into the opening in the body tissue. As the retracted outer sleeve 58a is moved into the opening in the body tissue, the external thread convolution 180 is moved into engagement with the body tissue. When this occurs, a suitable tool is utilized to apply a rotational force to the proximal end portion 68a of the outer fastener assembly 36a. The tool engages wrenching flats formed in the proximal end portion 68a of the outer sleeve 58a. The wrenching flats have the same construction as the wrenching flats 84 of FIG. 2.

As the outer sleeve 58a (FIG. 9) is rotated relative to the body tissue by the application of rotational force to the proximal end portion 68a of the outer sleeve, the external thread convolution 180 engages the body tissue and starts to cut an internal thread convolution in the body tissue. Thus, the external thread convolution 180 functions as a self-tapping thread to form an internal thread convolution as the external thread convolution is rotated relative to the body tissue by the application of rotational force to the proximal end portion 68a of the outer sleeve 58. The three leading turns of the external thread convolution 180 are axially tapered to facilitate engagement of the external thread convolution with the body tissue and initiation of the formation of an internal thread convolution in the body tissue. Continued rotation of the outer sleeve 58*a* results in increased engagement of the external thread convolution 180 with the body tissue and an increasing extent of the internal thread convolution formed in the body tissue by the external thread convolution.

As the outer sleeve 58*a* continues to be rotated, the smooth bulbous surface 184 on the proximal end portion 68*a* moves into engagement with the body tissue. Continued rotation of the outer sleeve 58*a* results in the body tissue being pressed firmly against the smooth outer surface 184 on the proximal end portion 68*a* of the outer sleeve. This results in the formation of a seal between the proximal end portion 68*a* of the outer sleeve 58*a* and the body tissue.

Once the retracted outer sleeve 58*a* (FIG. 9) has been installed in body tissue, the retracted outer sleeve is extended. To extend the outer sleeve 58*a*, a gripper, corresponding to the gripper 110 of FIG. 1, grips a projecting end portion 82*a* of the retracted outer sleeve 58*a*. At the same time, an actuator member, corresponding to the actuator member 112 of FIG. 4, is telescopically inserted into a central opening, corresponding to the central opening 116 of FIG. 2, in the outer sleeve 58*a*.

As this occurs, the actuator member nose end portion, corresponding to the nose end portion 120 of FIG. 5, engages cam surfaces, corresponding to the cam surfaces 124 of FIG. 7, on the arm sections 48*a*. The rightward (as viewed in FIG. 9) force applied against the arm sections 48*a* by the nose end portion of the actuator member, corresponding to the actuator member 112 of FIG. 5, causes the arm sections 48*a* to be forced radially outwardly from their retracted position, corresponding to the retracted position of the arms 48 in FIG. 2, to the extended condition illustrated in FIG. 9. During movement of the arm sections 48*a* to their extended positions, the body tissue 32 is moved by the arm sections. As the leftward (as viewed in FIG. 9) force is applied against the arm sections 48*a* by the actuator member, corresponding to the actuator member 112 of FIG. 5, the gripper, corresponding to the gripper 110 of FIG. 1, pulls the projecting end portion 82*a* of the outer sleeve 58*a* toward the left (as viewed in FIG. 9) to offset the rightward force applied to the arm sections 48*a* by the actuator member.

Once the outer sleeve 58*a* has been positioned in the body tissue and operated to the extended condition of FIG. 9, the actuator member is withdrawn from the outer sleeve. An inner fastener assembly 38*a* is then telescopically inserted into the outer sleeve 58*a*. As this occurs, a retracted inner sleeve 62*a* is telescopically inserted into the outer sleeve 58*a*. While the retracted inner sleeve 62*a* is telescopically inserted into the outer sleeve 58*a*, the outer sleeve is held against movement relative to body tissue by a gripper, corresponding to the gripper 110.

Continued axial movement of the inner sleeve 62*a* into the outer sleeve 58*a* moves an external thread convolution, on the proximal end portion of the inner sleeve 62*a* into engagement with an internal thread convolution on the proximal end portion 68*a* of the outer sleeve 58*a*. The external thread convolution on the proximal end portion of the inner sleeve 62*a* corresponds to the external thread convolution 92 on the inner sleeve 62 (FIGS. 3 and 4). The internal thread convolution on the proximal end portion 68*a* of the outer sleeve 58*a* corresponds to the internal thread convolution 93 (FIG. 4) on the external sleeve 58.

Once this has occurred, wrenching flats, corresponding to the wrenching flats 96 on the inner sleeve 62 of FIG. 3, are engaged by a suitable tool and the inner sleeve is rotated relative to the outer sleeve 58*a*. The outer sleeve 58*a* is held against rotation relative to the body tissue by a gripper, corresponding to a gripper 110 of FIG. 1. The gripper engages the projecting end portion 82*a* (FIG. 9) of the outer sleeve 58*a*. Rotation of the inner sleeve 62*a* relative to the outer sleeve 56*a* causes the external thread convolution on the proximal end portion of the inner sleeve to tightly engage the internal thread convolution on the outer sleeve in the same manner as previously described in connection with FIG. 4.

In the foregoing description, the outer sleeve 58*a* was extended before the retracted inner sleeve 62*a* was inserted into the outer sleeve. If desired, the retracted inner sleeve 62*a* may be utilized to extend the outer sleeve 58*a*. If this is done the distal end portion 44*a* of the retracted outer sleeve 62*a* would apply force against the cam surfaces on the arm sections 48*a*. This force would pivot the arm sections 48*a* radially outward to there extended positions and deflect body tissue adjacent to the arm sections.

After the inner sleeve 62*a* has been telescopically inserted into the outer sleeve 58*a* and connected to the outer sleeve, the inner sleeve 62*a* is extended. To extend the inner sleeve 62*a*, an actuator member, corresponding to the actuator member 144 of FIG. 6, is telescopically inserted into the inner sleeve 62*a*. The nose or leading end portion of the actuator member applies a rightward (as viewed in FIG. 9) force against arm sections 50*a* of the inner sleeve 62*a*. At the same time, the gripper, corresponding to the gripper 110 of FIG. 1, applies a leftward (as viewed in FIG. 9) force to the outer sleeve 58*a* to hold the interconnected inner and outer sleeves 58*a* and 62*a* against movement relative to the body tissue. The force applied against the arm sections 50*a* by the actuator member causes the arm sections to move radially outward to the expanded positions illustrated in FIG. 9 in the manner previously explained in conjunction with the embodiment of the invention illustrated in FIGS. 1-8. As the arm sections 50*a* move to their extended positions, the arm sections deflect body tissue.

The actuator member, corresponding to the actuator member 144 of FIG. 6, is then withdrawn from the inner sleeve 62*a*. A retainer member 54*a* (FIG. 9) is then telescopically inserted into the inner sleeve 62*a*. An external thread convolution on the retainer member 54*a*, corresponding to the external thread convolution 160 of FIG. 8, then engages an internal thread convolution, corresponding to the internal thread convolution 164 of FIG. 3, on the inner sleeve 62*a* to interconnect the retainer member 54*a* and the inner sleeve 62*a*. The retainer member 54*a* holds the arm sections 50*a* in their extended positions, illustrated in FIG. 9. At the same time, the arm sections 48*a* of the outer sleeve 58*a* are held in their extended positions by engagement with the inner sleeve 62*a*.

Once the fastener assembly 30*a* has been positioned in body tissue in the manner previously explained, the fastener assembly is held a desired position relative to the body tissue by engagement of the external thread convolution 180 (FIG. 9) with the body tissue. The fastener assembly 30*a* is also is held against movement relative to the body tissue by engagement of the arm sections 48*a* and bulbous surface 184 on the proximal end portion 68*a* of the outer sleeve 58*a* with body tissue. In addition, the fastener assembly 30*a* is held against movement relative to the body tissue by engagement of the arm sections 50*a* on the inner sleeve 62*a* with the body tissue.

External Thread Convolution—Inner Fastener Assembly

In the embodiment of the invention illustrated in FIG. 9, the external thread convolution 180 is disposed on the outer fastener assembly 36*a*. In the embodiment of the invention illustrated in FIG. 10, an external thread convolution is disposed on the inner fastener assembly. Since the embodiments of the invention illustrated in FIGS. 1-9 are generally similar to the embodiment of FIG. 10, similar numerals will be utilized to designate similar components, the suffix letter "b" being associated with the numerals of FIG. 10 to avoid confusion.

A fastener apparatus 30b includes an outer fastener assembly 36b and an inner fastener assembly 38b (FIG. 10). The outer fastener assembly 36b includes an outer sleeve 58b having a proximal end portion 68b. The proximal end portion 68b of the outer sleeve 58b has a smooth convex bulbous outer side surface 184b. If desired, the proximal end portion 68b may have a different configuration, such as the configuration illustrated in FIGS. 1 and 2. A projecting end portion 82b of the outer sleeve 58b is engageable by a gripper in the same manner as previously described in conjunction with the embodiment of the invention illustrated in FIG. 1.

The outer sleeve 58b (FIG. 10) is inserted into body tissue with arm sections 48b retracted. After the arm sections 48b have been moved to the extended condition shown in FIG. 10, the inner sleeve 62b is telescopically inserted into the outer sleeve 58b. The inner sleeve 62b does not have extendable arm sections, corresponding to the arm sections 50a of FIG. 9. However, if desired, the inner sleeve 62b (FIG. 10) could be formed with extendable arm sections. If this was done, a portion of an external thread convolution 200 would move with the arm sections as the arm sections are extended. This would result in a portion of the external thread convolution 200 being moved relative to body tissue when the arm sections are moved from a retracted condition to an extended condition by insertion of an actuator member, corresponding to the actuator member 144 of FIG. 6, into the inner sleeve 62b in the manner previously explained in conjunction with the embodiments of the invention illustrated in FIG. 1-9.

In accordance with a feature of the embodiment of the invention illustrated in FIG. 10, the external thread convolution 200 engages body tissue to anchor the fastener assembly 30b in the body tissue. The external thread convolution 200 has a tapered leading end portion 188b and a cylindrical main portion 190b. The tapered leading end portion 188b is formed on a leading end 206 of the inner sleeve 62b. The leading end 206 of the inner sleeve 62b has a configuration corresponding to the configuration of a right circular cone.

The tapered leading end portion 188b of the external thread convolution has a crest diameter which increases from the tip or apex of the leading end 206 of the inner sleeve 62b to a relatively uniform crest diameter at a location where the main portion 190b of the external thread convolution begins. The main portion 190b of the external thread convolution 200b has a constant crest diameter throughout its length. In addition, the main portion 190b of the external thread convolution 200 has a constant root diameter throughout its length.

The external thread convolution 200 is integrally formed as one piece with the inner sleeve 62b. However, if desired, the external thread convolution 200 may be formed separately from the inner sleeve 62b and connected with the inner sleeve. For example, the external thread convolution 200 may be formed on a tubular member, corresponding to the tube 194 of FIG. 9. If the external thread convolution 200 is formed on a tubular member, the tubular member would have a closed conical leading end on which the tapered leading end portion 188b of the external thread convolution would be formed. Tubular member on which the external thread convolution is formed would have a constant diameter cylindrical portion connected with the closed conical leading end. The main portion 190b of the external thread convolution would be disposed on the constant diameter cylindrical portion of the tubular member.

The tubular member on which the external thread convolution is formed may be formed of a metal which is the same as the metal of the inner sleeve 62b, that is, stainless steel or titanium. If desired, the tubular member may be formed of a suitable polymeric material. If this was done, the external thread convolution 200 would be formed of the same polymeric material or may be formed of metal. It is believed that it may be desired to form the external thread convolution 200 as one piece with the metal inner sleeve 62b, in the manner illustrated in FIG. 10, in order to facilitate construction of the inner sleeve 62b.

When the fastener assembly or apparatus 30b (FIG. 10) is to be installed in body tissue, similar to the body tissue 32 of FIG. 1, an opening is formed in the body tissue. When the body tissue 32 is hard (bone), a hole having a diameter which is about the same as the diameter of the cylindrical outer side surface of the central portion 66b may be drilled in the bone. When the body tissue 32 is soft body tissue, an opening may be cut in the body tissue.

When the fastener apparatus 30b is to be installed in body tissue, the outer sleeve 58b is first positioned in the body tissue. With the outer sleeve 58b in a retracted condition, corresponding to the retracted condition of the outer sleeve 58 in FIG. 2, the distal end portion 42b of the outer sleeve 58b is moved into an opening in the body tissue. As a retracted outer sleeve 58b is moved into the opening in the body tissue, the smooth bulbous surface 184b on the proximal end portion 68b of the outer sleeve 58b moves into engagement with the body tissue.

The distal end portion 42b of the outer sleeve 58b is then expanded by insertion of an actuator member, corresponding to the actuator member 112 of FIG. 5, into the outer sleeve 58b. As the actuator member is inserted into the outer sleeve 58b, a gripper, corresponding to the gripper 110 of FIG. 1, grips the projecting end portion 82b of the outer sleeve 58b to hold the outer sleeve against movement relative to the body tissue. As the actuator member is inserted into the outer sleeve 58b, the arm sections 48b are pivoted radially outwardly from their retracted positions to the extended positions illustrated in FIG. 10. The manner in which this is accomplished is the same as was previously described in conjunction with the embodiments of the invention illustrated in FIGS. 1-9. The actuator member is then withdrawn from the extended outer sleeve 58b.

The inner sleeve 62b (FIG. 10) is then telescopically inserted into the extended outer sleeve 58b. As the leading end 206 of the inner sleeve 62b moves into alignment with the extended arm sections 48b on the outer sleeve 58b, the tapered leading end portion 188b of the external thread convolution 200 on the inner sleeve moves into engagement with body tissue.

Once the leading end 206 of the inner sleeve 62b has engaged the body tissue, a suitable tool is moved into engagement with wrenching flats, corresponding to wrenching flats 96 of FIG. 3, on the proximal end portion of the inner sleeve 62b. The tool is then rotated to rotate the inner sleeve 62b relative to the outer sleeve 58b. As the inner sleeve 62b is rotated relative to the outer sleeve 58b, a gripper, corresponding to the gripper 110 of FIG. 1, engages the projecting portion 82b of the outer sleeve 58b to hold the outer sleeve against movement relative to the body tissue.

As the inner sleeve 62b is rotated, the tapered leading end portion 188b of the external thread convolution 200 cuts into the body tissue and initiates the formation of an internal thread convolution in the body tissue. Continued rotation of the inner sleeve 62b relative to the outer sleeve 58b and body tissue moves the main portion 190b of the external thread convolution 200 into engagement with the body tissue. Further rotation of the inner sleeve 62b relative to the outer sleeve 58b and body tissue causes the inner sleeve 62b to move rightward (as viewed in FIG. 10) relative to the outer sleeve 58b.

As this occurs, an external thread convolution, corresponding the external thread convolution 92 of FIG. 3, on the proximal end portion of the inner sleeve 62b moves into engagement with an internal thread convolution, corresponding to the internal thread convolution 93 of FIG. 4, on the proximal end portion 68b of the outer sleeve 58b. Continued rotation of the inner sleeve 62b results in continued rightward movement of the inner sleeve 62b relative to the outer sleeve 58b. The inner and outer sleeves 62b and 58b are interconnected by engagement of the external thread convolution on the proximal end portion of the inner sleeve with the internal thread convolution on the proximal end portion of the outer sleeve. At the same time, the external thread convolution 200 (FIG. 10) has moved into secure engagement with the body tissue which is engaged by the external thread convolution.

Fastener Apparatus—External Thread Convolution

In the embodiment of the invention illustrated in FIG. 11, a fastener apparatus having only a single sleeve is provided with an external thread convolution. Since the embodiment of the invention illustrated in FIG. 11 is general similar to the embodiments of the invention illustrated in FIGS. 1-10, similar numerals will be utilized to designate similar components, the suffix letter "c" being associated with the numerals of FIG. 11 to avoid confusion.

A fastener or apparatus 30c includes a fastener assembly 36c having a construction general similar to the construction of the outer fastener assembly 36a of FIG. 9. The fastener assembly 36c includes a cylindrical outer sleeve 58c having a distal end portion 42c and a conical proximal end portion 68c. The distal end portion 42c has the same construction as the distal end portion 42 of the outer fastener assembly 36 of FIGS. 1 and 2. Similarly, the proximal end portion 68c has the same construction as the proximal end portion 68 of the outer fastener assembly 36 of FIGS. 1 and 2.

An external thread convolution 180c is fixedly connected with the outer sleeve 58c. The external thread convolution 180c is formed of the same material as the outer sleeve 58c. Thus, both the outer sleeve 58c and external thread convolution 180c may be formed of a suitable biocompatible metal, such as stainless steel or titanium. Alternatively, the outer sleeve 58c and external thread convolution 180c may be formed of different materials. For example, the external thread convolution 180c may be formed of a polymeric material.

The external thread convolution 180c includes a tapered leading end portion 188c and a main portion 190c. Throughout the axial extent of the main portion 190c, it has uniform crest and root diameters. The tapered leading end portion 188c of the external thread convolution 180c has a uniform root diameter which is the same as the root diameter of the main portion 190c of the external thread convolution. However, the leading end portion 188c of the external thread convolution 180c has a crest diameter which increases from a relatively small diameter at the leading or right (as viewed in FIG. 11) end of the external thread convolution 180c. The crest diameter of the tapered leading end portion 188c of the external thread convolution 180c increases from a relatively small diameter to the same diameter as the main portion 190c of the external thread convolution 180c to facilitate engagement of the external thread convolution with body tissue.

The external thread convolution 180c is fixedly mounted on a cylindrical tube 194c. The cylindrical tube 194c is telescopically received on and is fixedly connected to the outer sleeve 58c. The external thread convolution 180c and tube 194c may have the same construction as previously described in conjunction with the external thread convolution 180 and tube 194 of FIG. 9.

In the embodiment of the invention illustrated in FIG. 11, a retainer 54c is disposed within the outer sleeve 58c. The retainer 54c has an external thread convolution, corresponding to the external thread convolution 160 on the retainer 54 of FIG. 8, which engages a correspondingly configured internal thread convolution on the outer sleeve 58c. The retainer 54c holds arm sections 48c of the external sleeve 58c in their extended positions, illustrated in FIG. 11. The retainer 54c may be utilized to operate the outer sleeve 58c from a retracted condition to the illustrated extended condition.

When the fastener apparatus 30c is to be connected with body tissue, the outer sleeve 58c is in its initial condition with the arm sections 48c in their retracted positions, corresponding to the retracted positions of the arm sections 48 of FIG. 2. An opening is formed in the body tissue into which the fastener apparatus 30c is to be inserted. The retracted distal end portion 42c of the outer sleeve 58c is inserted into the opening in the body tissue. As this occurs, the body tissue moves into engagement with the leading turn of the tapered leading end portion 188c of the external thread convolution 180c.

A suitable tool is then moved into engagement with wrenching flats, corresponding to the wrenching flats 84 of FIG. 2, on the proximal end portion of 68c of the outer sleeve 58c. The tool applies torque to the outer sleeve 58c (FIG. 11) to rotate the external thread convolution 180c relative to the body tissue. As the outer sleeve 58c and external thread convolution 180c are rotated relative to the body tissue, the outer sleeve 58c and external thread convolution 180c move axially into the body tissue.

When the outer sleeve 58c has moved to a desired position relative to the body tissue, the proximal end portion 68c of the outer sleeve 58c is engaged by, a gripper, corresponding to the gripper 110 of FIG. 1. An actuator member, corresponding to the actuator member 112 of FIG. 5, is then telescopically inserted into the outer sleeve 58c and pressed against cam surfaces on the arm sections 48c. Force applied against the arm sections by the nose end portion of the actuator member pivots the arm sections 48c from their retracted positions to their illustrated extended positions and deflects body tissue in the manner previously described in conjunction with the embodiments of the invention illustrated in FIGS. 1-10. While force is applied against the arm sections 48c by the actuator member, the gripper pulls toward the left (as viewed in FIG. 11) on the projecting portion 82c of the outer sleeve 58c to offset the force applied to the outer sleeve by the actuator member.

After the arm sections 48c have been moved to their extended positions and the actuator member withdrawn from the outer sleeve 58c, the retainer member 54c (FIG. 11) is telescopically moved into the outer sleeve 58c. The retainer member 54c has the same construction as the retainer member 54 of FIG. 8. Therefore, as the retainer member 54c moves into the outer sleeve, an external thread convolution, corresponding to the external thread convolution 160 on the retainer member 54 of FIG. 8, moves into engagement with an internal thread convolution in the outer sleeve 58c. The retainer member is then rotated relative to the outer sleeve to engage the external thread convolution on the retainer member 54c with the internal thread convolution in the outer sleeve 58c. Once the retainer member 54c has been moved to the position illustrated in FIG. 11. The retainer member 54c holds the arm sections 48c in the illustrated extended positions.

As was previously mentioned, the retainer member 54c may be utilized to expand the outer sleeve 58c to the extended condition of FIG. 11. When this is to be done, the retracted outer sleeve 58c is positioned in the body tissue in the manner previously explained. The retainer member 54c is then telescopically inserted into the outer sleeve 58c while the outer sleeve is held by a gripper, corresponding to the gripper 110 of FIG. 1. As the retainer member 54c is inserted into the outer sleeve 58c, an external thread convolution, corresponding to the external thread convolution 160 of FIG. 8, moves into engagement with an internal thread convolution, corresponding to the internal thread convolution 164 of FIG. 3.

The retainer member 54c is then rotated relative to the outer sleeve 58c. Engagement of the external thread convolution on the retainer member with the internal thread convolution on the stationary outer sleeve 58c results in the nose end portion 166c of the retainer member 54c being pressed against the cam surfaces on the arm sections 48c. The force applied against the arm sections 48c by the retainer member 54c is effective to pivot the arm sections to their extended positions (FIG. 11). As the arm sections 48c move to there extended positions, the arm sections are pressed against and move body tissue.

In the embodiment of FIG. 11, there is only one sleeve, that is, the outer sleeve 58c. However, a second or inner sleeve, corresponding to the inner sleeve 62a of FIG. 9, may be provided. If desired, an even greater number of sleeves may be provided.

Fastener Apparatus—External Ribs

In the embodiment of the invention illustrated in FIG. 11, an external thread convolution 180c is associated with the fastener apparatus 30c. In the embodiment of the invention illustrated in FIG. 12, external ribs are provided in association with the fastener apparatus. Since the embodiment of the invention illustrated in FIG. 12 is generally similar to the embodiments of the invention illustrated in FIGS. 1-11, similar numerals will be utilized to designate similar components, the suffix letter d" being associated with the numerals of FIG. 12 to avoid confusion.

A fastener apparatus 30d includes an outer fastener assembly 36d. The outer fastener assembly 36d includes an outer sleeve 58d. The outer sleeve 58d includes a cylindrical central portion 66d. A distal end portion 44d is disposed to the right (as viewed in FIG. 12) of the central portion 66d. Similarly, a conical proximal end portion 68d is disposed to the left of the central portion 66d.

Figure 12:
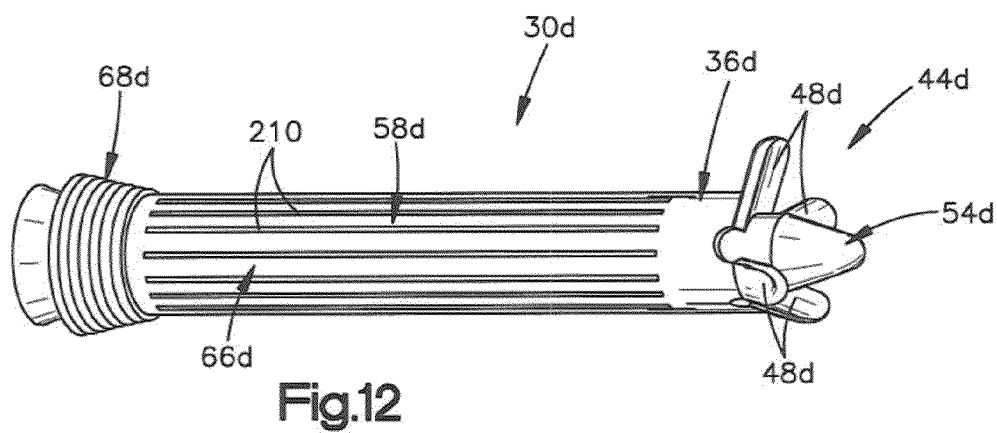
FIG. 12 is a schematic pictorial illustration of a fastener assembly or apparatus having a sleeve with ribs.

The distal end portion 44d of the outer sleeve 58d includes arm sections 48d which are movable from retracted positions, corresponding to the retracted positions of the arm sections 48 in FIG. 2, to extended positions, illustrated in FIG. 12. The arm sections 48d are held in their extended positions by a retainer member 54d. The manner in which the arm sections 48d are moved to their extended positions and the manner in which the retainer member 54d holds the arm sections in their extended positions is the same as was previously described in conjunction with the embodiments of the invention illustrated in FIGS. 1-11.

In accordance with a feature of the embodiment of the invention illustrated in FIG. 12, ribs 210 are provided on the central portion 66d of the outer sleeve 58d. The ribs 210 engage body tissue, corresponding to the body tissue 32 of FIG. 1, to hold the outer sleeve 58d against rotation of movement relative to the body tissue. The straight ribs 210 project radially outward from a cylindrical outer side surface of the central portion 66c. The ribs 210 have longitudinal central axes which extend parallel to the longitudinal central axis of the outer sleeve 58d.

In the embodiment of the invention illustrated in FIG. 12, the ribs 210 have a substantially uniform cross sectional configuration. However, it is contemplated that the ribs 210 could be provided with a non-uniform cross sectional configuration. For example, each of the ribs 210 may be formed by a series of pyramidal shaped projections. The pyramidal projections may all be formed with the same height or have different heights. Of course, the ribs 210 may have a different configuration if desired. For example, a series of barbs may be formed at spaced apart intervals along the ribs 210 to engage the body tissue.

In the embodiment of the invention illustrated in FIG. 12, the uniform ribs 210 extend parallel to each other and to the longitudinal central axis of the outer sleeve 58d. It is contemplated that the ribs 210 may extend transverse to the longitudinal central axis of the outer sleeve 36d. Thus, each of the ribs 210 may be formed with a helical configuration so that it wraps around the outer sleeve 36d. If desired, the ribs 210 may be formed with helical configurations and wrapped in different directions around the outer sleeve 58d. For example, some of the ribs 210 may have a helical configuration and be wrapped around the outer sleeve 58d in a clockwise direction while other ribs are formed with a helical configuration and are wrapped in a counterclockwise direction around the outer sleeve 58d.

Fastener Apparatus—Porous Outer Surface

Figure 13:
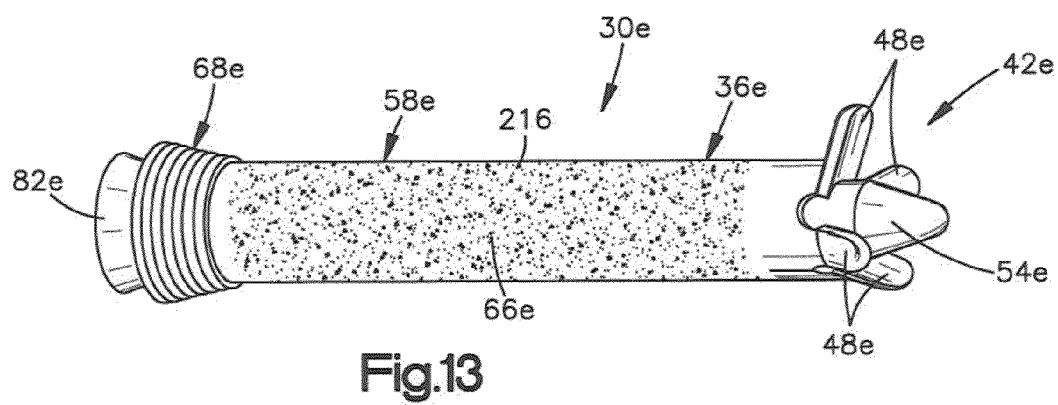
FIG. 13 is a schematic pictorial illustration of a fastener assembly or apparatus having a sleeve with a porous outer surface.

In the embodiment of the invention illustrated in FIG. 13, the fastener apparatus has a porous outer side surface to promote tissue in-growth. Since the embodiment of the invention of FIG. 13 is generally similar to the embodiments of the invention illustrated in FIGS. 1-12, similar numerals will be utilized to designate similar components, the suffix letter "e" being associated with the numerals of FIG. 13.

A fastener apparatus 30e includes an outer fastener assembly 36e having an outer sleeve 58e. The outer sleeve 58e has a central portion 66e which extends between a distal end portion 42c and a conical proximal end portion 68e. The distal end portion 42e includes a plurality of arm sections 48e which are held in the extended position illustrated in FIG. 13 by a retainer member 54e. The distal end portion 68e includes a projecting end portion 82e which is engageable by a gripper corresponding to the gripper 110 of FIG. 1.

In accordance with a feature of the embodiment of the invention illustrated in FIG. 12, the outer sleeve 58e has a porous surface 216 which promotes tissue in-growth. The porous outer surface 216 may be integrally formed as one piece with the remainder of the outer sleeve 58e. Alternatively, the porous outer surface 216 may be formed as a portion of a tube which is telescopically positioned on and fixedly connected to the outer sleeve 58e. If desired, tissue growth inducing materials may be embedded in the material forming the porous surface 216.

In the embodiment of the invention illustrated in FIG. 13, the material forming the porous surface 216 extends through only a portion of the thickness of the outer sleeve 58e. However, if desired, the material forming the porous surface 216 may extend radially through the outer sleeve to an inner side surface, corresponding to the inner side surface 130 of FIG. 2.

Implants

It is contemplated that the fastener apparatus of FIGS. 1-13 may be utilized in association with implants in a patient's body or may be positioned directly in tissue in a patient's body. The manner in which the fastener apparatus of FIGS. 1-13 may be utilized with certain known implants has been illustrated schematically in FIGS. 14 through 19. It should be understood that the illustrated implants are merely representative of many different implants with which the fastener apparatus of FIGS. 1-13 may be utilized.

A fastener apparatus 30 having the same construction as illustrated in FIGS. 1-8 is illustrated in FIG. 14 in association with a plate 224 which is to be implanted in a patient's body. The plate 224 may be mounted on a bone in a patient's body. For example, the plate 224 may be utilized in association with a femur.

The plate 224 includes a flat, generally rectangular, main section 226 in which a plurality of holes 228 are formed to receive fasteners. The fasteners disposed in the holes 228 may have the same construction as any one the fasteners disclosed in FIGS. 1-13. Alternatively, the fasteners which are received in the holes 228 may be conventional bone screws.

A cylindrical stabilizing section 232 extends from the plate 224. The fastener apparatus 30 extends through the hollow stabilizing section 232 and has a proximal end portion, corresponding to the proximal end portion 68 of FIG. 1, which is received in an opening 234 in the plate 224. The proximal end portion of the fastener apparatus 30 has an external thread convolution, corresponding to the external thread convolution 78 of FIG. 2, which engages a similarly shaped internal thread convolution on the plate 224. If desired, the fastener apparatus 30 and plate 224 may be interconnected in a different manner. For example, a locking lug on the fastener apparatus 30 or the plate 224 may engage a retaining surface. Alternatively, a locking clip may be used to interconnect the fastener apparatus 30 and plate 224.

The tubular stabilizing section 232 is fixedly connected to the plate 224 and has a longitudinal central axis which intersects a longitudinal central axis of the plate 224 at an obtuse angle. The fastener apparatus 30 extends through and is coaxial with the stabilizing section 232. The external thread on the proximal end portion, corresponding to the proximal end portion 68 of FIGS. 1 and 2, of the fastener apparatus 30 engages as similarly shaped internal thread convolution at the periphery of the opening 234 in the plate 224. To interconnect the external thread convolution on the proximal end portion of the fastener apparatus 30 (FIG. 14) with the internal thread convolution on the plate 224, the retracted outer sleeve 58 is rotated relative to the plate.

The stabilizing section 232 has a cylindrical inner side surface which engages the cylindrical outer side surface of the central portion 66 of the outer sleeve 58 throughout the extent of the inner side surface of the stabilizing section. Abutting engagement of the outer side surface of the central portion 66 (FIGS. 1 and 2) of the outer sleeve 58 with the inner side surface of the stabilizing section 232 is effective to position the fastener 30 so that it is securely supported in a desired position relative to the plate 224. The longitudinal central axis of the fastener apparatus 30 is maintained coincident with the longitudinal central axis of the stabilizing section 232 by engagement of the outer sleeve 58 with the stabilizing section. The stabilized fastener apparatus 30 is disposed at the same obtuse angle to the longitudinal central axis of the plate 224 as is the central axis of the stabilizing section 232.

The fastener apparatus 30 is connected with body tissue, that is, bone with which the plate 224 is associated, by the extended arm sections 48 of the outer sleeve 58 and by the extended arm sections 50 of the inner sleeve 62. The arm sections 48 of the outer sleeve 58 are held in their extended positions by engagement with the inner sleeve 62 in the manner previously explained in conjunction with the embodiment of the invention illustrated in FIGS. 1-8. The arm sections 50 are maintained in their extended positions by engagement with the retainer member 54. The extended arm sections 48 and 50 engage bone in a patient's body to securely hold the plate 224 in position relative to the patient's body.

Although a plate 224 having one specific construction has been illustrated schematically in FIG. 14, it is contemplated that the bone plate 224 may have a different construction if desired. For example, the bone plate 224 may have a construction similar to the constructions disclosed in U.S. Pat. Nos. 4,955,886 and/or 6,096,040. It is contemplated that the plate 224 may have any one of many different constructions depending upon the location where the plate is to be positioned in a patient's body. For example, if the plate 224 is associated with the bone in an arm of a patient, the plate would have a construction which facilitates use of the plate in association with the patient's arm.

In the embodiment of the invention illustrated in FIG. 15, fastener apparatuses constructed in accordance with FIGS. 1-13 are schematically illustrated in association with an end intramedullary nail 240. The nail 240 is positioned within a patient's bone. Thus, the nail 240 may engage cancellous material in the patient's bone.

A fastener apparatus 30 (FIG. 15) is utilized to connect the nail 240 with cortical and/or cancellous bone. The fastener apparatus 30 has the same construction as is illustrated in FIGS. 1-8. The fastener apparatus 30 includes an outer fastener assembly 36 having a proximal end portion 68 which is secured to hard cortical bone. The fastener apparatus 30 extends through the nail 240 and has a longitudinal central axis which intersects the longitudinal central axis of the intramedullary nail 240 at an obtuse angle. A portion of the outer sleeve 58 between the proximal end portion 68 and the distal end portion 42 engages side surfaces of an opening in the nail 240 to position the fastener apparatus 30 in a desired orientation relative to the nail.

The outer sleeve 58 of the fastener apparatus 30 has extended arm sections 48 which engage cancellous and/or cortical bone in a patient's body. Similarly, an inner sleeve 62 of the fastener apparatus 30 has extended arm sections 50 which engage cancellous or cortical bone in the patient's body. The arm sections 48 are held in their extended positions by engagement with the inner sleeve 62. Similarly, the arm sections 50 are held in their extended positions by engagement with a retainer member 54.

In the embodiment schematically illustrated in FIG. 15, the inner sleeve 62 extends for a substantial distance from the arm sections 48 of the outer sleeve 58. Depending upon the location where the intramedullary nail 240 is used, the inner sleeve 62 may have a shorter axial extent so that the extended arm sections 50 are closer to the extended arm sections 48.

A second fastener apparatus 244 is schematically illustrated in association with a lower (as viewed in FIG. 15) end portion of the intramedullary nail 240. The fastener apparatus 244 has the same general construction as the fastener apparatus of FIGS. 1-13. However, the fastener apparatus 244 includes only an outer fastener assembly 36. Therefore, the apparatus 244 has only an outer sleeve 58 which extends through an opening in the lower (as viewed in FIG. 15) end portion of the intramedullary nail 240.

The proximal end portion 68 of the fastener apparatus 244 engages cortical bone on one side of the intramedullary nail 240. Arm sections 48 of the outer sleeve 58 of the fastener apparatus 244 are illustrated in their extended positions. The arm sections 48 of the outer sleeve 58 of the fastener apparatus 244 are held in their extended positions by engagement with a retainer 54.

The illustrated fastener apparatus 244 has a construction generally similar to the construction of the fastener apparatus 30d of FIG. 12. However, the ribs 210 may, if desired, be omitted from the outer sleeve 58 of the fastener apparatus 244. Of course, the fastener apparatus 244 may have a different construction if desired.

The intramedullary nail 240 has a known construction which is generally similar to the constructions disclosed in U.S. Pat. Nos. 5,653,709; 6,010,505 and/or 6,228,086. Of course, the intramedullary nail 240 may have a construction which differs from the construction disclosed in the aforementioned patents.

In the embodiment of FIGS. 16 and 17, fastener apparatus constructed in accordance with the present invention are utilized in association with an implant designed to replace a portion of a joint in a patient's body. An apparatus 250 (FIGS. 16 and 17) includes an implant 252. The implant 252 is a socket joint replacement cup. The schematically illustrated implant 252 is held in a desired position in a patient's body by a plurality of fastener apparatuses 254 and 256. Although only two fastener apparatuses 254 and 256 are schematically illustrated in FIGS. 16 and 17, it should be understood that additional fastener apparatuses may be associated with the implant 252 if desired.

The fastener apparatus 254 has the same construction as the fastener apparatus 30e of FIG. 13. Thus, the fastener apparatus 254 includes an outer sleeve 58e having a porous outer surface 216 into which bone can grow. A proximal end portion (not shown) of the fastener apparatus 254 engages a periphery of an opening in the implant 252 to position the fastener apparatus relative to the implant. An external thread convolution on the proximal end portion of the fastener apparatus 254 engages an internal thread convolution on the implant 252 to interconnect the fastener apparatus and implant. Arm sections 48e of the fastener apparatus 254 engage bone in the patient's body to anchor the implant 252 in place.

The fastener apparatus 256 has a construction which corresponds to the construction of the fastener apparatus 30c of FIG. 11. The proximal end portion 68c (FIG. 11) of the fastener apparatus 256 (FIGS. 16 and 17) engages the implant 252 to position the fastener apparatus 30c relative to the implant. The fastener apparatus 30c includes an external thread convolution 180c which engages bone in a patient's body to retain the implant 252 against movement relative to the bone.

Although specific fastener apparatuses 254 and 256 have been schematically illustrated in association with the implant 252, it is contemplated that any one of the fastener apparatuses disclosed herein may be utilized in association with the implant 252. The implant 252 is used in association with a socket joint replacement. The implant 252 may be utilized in association with either a hip joint or shoulder joint replacement.

The implant 252 may be designed to be utilized in association with other joints in a patient's body. It is contemplated that the implant 252 will have a design which is specific to the location where it is to be utilized in the patient's body. For example, the implant 252 may have a design similar to the design disclosed in U.S. Pat. Nos. 5,413,603 and/or 6,010,535.

A bone plate implant apparatus 262 is illustrated in FIG. 18. The bone plate implant apparatus 262 includes a plate 266. The plate 266 has a generally T-shaped configuration with a head portion 268 which is connected to an elongate body portion 270 by a neck portion 272. A plurality of holes 276 are disposed in a linear array in the head portion 268. In addition, a plurality of holes 278 are formed in the body portion 270 of the bone plate 262.

A plurality of fastener apparatuses 284 are provided in association with the holes 276. Although only three fastener apparatuses 284 have been schematically illustrated in association with the four holes 276, it is contemplated that an additional fastener apparatuses will be provided in association with the fourth or more holes. Of course, a greater or lesser number of holes 276 and fastener apparatuses 284 may be provided if desired.

The fastener apparatuses 284 have the same general construction as the fastener apparatus 30d of FIG. 12. The fastener apparatuses 284 have proximal end portions 60d which engage the peripheries of the holes 276. The proximal end portions 60d of the fastener apparatuses 284 are formed as portions of spheres which engage similarly shaped sockets at the peripheries of the holes 276. Unlike the outer sleeve 58d of FIG. 12, the outer sleeves of 58d of FIG. 18 do not have ribs, corresponding to the ribs 210 of FIG. 12. However, if desired, ribs may be provided on the outer sleeves 58d of FIG. 18.

Each of the outer sleeves 58d has a plurality of arm sections 48d which are held in the illustrated extended positions by retainers 54d. Although fastener apparatuses 284 have been schematically illustrated in FIG. 18 in association with only the holes 276, it is contemplated that similar fastener assemblies may be used in association with the holes 278. Alternatively, conventional bone screws may be utilized in association with the holes 278 if desired.

The fastener apparatuses 284 may have the same construction as any one of the fastener apparatuses of FIGS. 1 through 13. For example, the fastener apparatuses 284 may have the construction illustrated in FIG. 1 with a plurality of sleeves and arm sections. Although only two sleeves, that is, the outer sleeve 58 and inner sleeve 52 have been illustrated in FIG. 1, it should be understood that a greater or lesser number of sleeves may be provided in association with the fastener apparatuses 284 if desired.

The bone plate implant apparatus 262 may be utilized in association with the arm and hand of a patient. However, the bone plate implant apparatus may be designed so as to be utilized with a shoulder, hip or foot of a patient if desired. It is contemplated that the bone plate apparatus 262 may have any desired configuration for association with any desired portion of a patient's body. The general construction of the bone plate apparatus 262 is similar to the construction illustrated in U.S. Pat. Nos. 6,712,820 and/or 7,001,388.

A femoral stem prosthesis 290 (FIG. 19) has a stem 292 which is inserted into a femur. A prosthetic 294 is fixedly connected with the stem portion 292. The prosthetic portion 294 has a neck 296 which receives a spherical head for engagement with a hip replacement.

A fastener apparatus 300 extends axially through the stem portion 292 and has the same general construction as the fastener apparatuses of FIGS. 1-13. The fastener apparatus 300 has a plurality of arm sections 48 which are held in the illustrated extended positions by a retainer member, corresponding to the retainer member 54 of FIG. 8. The extended arm sections engage a bone in which the stem portion 292 is inserted to thereby anchor the stem portion against movement relative to the bone. Of course, a suitable cement may also be used to anchor the stem portion 292. Although only a single array of arm sections 48 has been illustrated schematically in FIG. 19, it should be understood that a plurality of arrays of arm sections may be provided in association with the fastener apparatus 300.

It is contemplated that the femoral prosthesis 290 may have any one of many different constructions. For example the femoral prosthesis may be constructed in the manner disclosed in U.S. Pat. Nos. 4,770,660; 4,908,035; 5,290,318; and/or 7,004,973. It should be understood that the femoral prosthesis 290 may have any one of many known constructions. Regardless of the specific construction of the femoral prosthesis 290, the use of the fastener apparatus 300 in association with the femoral prosthesis 290 will enable the prosthesis to securely grip the bone and hold the stem portion 292 in the bone.

Fastener Apparatus Outer Sleeve

In the embodiment of the invention illustrated in FIGS. 20-22, a fastener apparatus having an outer sleeve with an external thread convolution, an alternative distal end portion, and an alternative proximal end portion is illustrated. Since the embodiment of the invention illustrated in FIGS. 20-22 is generally similar to the embodiments of the invention illustrated in FIGS. 1-13, similar numerals will be utilized to designate similar components, the suffix letter "f" being associated with the numerals of FIGS. 20-22 to avoid confusion.

Although only an outer sleeve 58f of a fastener assembly 36f is illustrated in FIG. 20, it should be understood that the fastener assembly 36f includes an actuator member, corresponding to the actuator member 112 of FIG. 5. The actuator member is telescopically inserted into the outer sleeve 58f to pivot arm sections 48f from their retracted positions illustrated in FIGS. 20 and 21 to extended positions corresponding to the extended positions of the arm sections 48 in FIG. 1. Force applied against the arm sections 48f by the nose end portion of the actuator member pivots the arm sections from their retracted positions to their extended positions and deflects body tissue in the manner previously described in conjunction with the embodiments of the invention illustrated in FIGS. 1-13.

After the arm sections 48f have been moved to their extended positions and the actuator member withdrawn from the outer sleeve 58f, a retainer member, similar to the retainer member 54 of FIG. 8, is telescopically moved into the outer sleeve 58f. As the retainer member moves into the outer sleeve 58l (FIG. 20), an external thread convolution, corresponding to the external thread convolution 160 on the retainer member 54 of FIG. 8, moves into engagement with an internal thread convolution in the outer sleeve 58f. The retainer member is then rotated relative to the outer sleeve 58f to engage the external thread convolution on the retainer member with the internal thread convolution on the outer sleeve 58f. Once the retainer member has been moved telescopically into the outer sleeve 58f and screwed into the outer sleeve, the arm sections 48f are held in their extended conditions.

Prior to movement of the actuator member into the outer sleeve 58f to move the arm sections 48f from their retracted positions illustrated in FIGS. 20 and 21 to their extended positions corresponding to the extended positions of the arm sections 48 and 50 of FIG. 1, a helical external thread convolution 180f on the outer sleeve 58f is moved into engagement with body tissue. The body tissue may be either hard body tissue or soft body tissue. The thread convolution 180f has a uniform root diameter throughout the extent of the thread convolution. Although the thread convolution 180f is integrally formed as one piece with the outer sleeve 58f, the thread convolution 180f may be formed on a cylindrical tube, corresponding to the cylindrical tube 194 of FIG. 9, if desired. Rather than having a single helical thread convolution on the central portion 66f of the outer sleeve 58f, a plurality of coaxial helical thread convolutions may be provided on the central portion 66f of the outer sleeve 58f.

The distal end portion 42f (FIG. 20) of the outer sleeve 58f includes identical arm sections 48f. The arm sections 48f are formed by a plurality of equal length slots 86f (FIG. 21) which extend radially outward from a central axis of the outer sleeve 58. In the embodiment of the invention illustrated in FIGS. 20 and 21, there are four arm sections 48f which are formed by two perpendicular slots 86f in the distal end portion 42f of the outer sleeve 58f. However, it should be understood that a greater or lesser number of arm sections 48f may be provided in the distal end portion 42f of the outer sleeve 58f if desired.

A flat outer side surface is formed on each of the arm sections 48f. The flat outer side surface 320 slopes axially outwardly from a base portion 324 to a tip portion 326 in the manner illustrated in FIG. 20. The flat side surfaces 320 facilitate movement of body tissue when the arms 48f are moved from their retracted positions to their extended positions. In addition, the flat outer side surfaces 320 facilitate gripping of body tissue by the arm sections 48f when the arm sections are in their extended positions.

The proximal end portion 68f (FIGS. 20 and 22) of the outer sleeve 58f includes wrenching flats 332 (FIG. 22) which may be engaged by a spanner wrench or similar tool to rotate the outer sleeve 58f about its longitudinal central axis. In addition, the proximal end portion 68f includes a smooth convex arcuate surface 184f. The proximal end portion 68f of the outer sleeve 58f is free of a thread convolution corresponding to the thread convolution 78 (FIG. 2). However, it is contemplated that a thread convolution, corresponding to the thread convolution 78 may be provided on the proximal end portion 68f of the outer sleeve 58f if desired.

Main and Secondary Fastener Assemblies

Figure 23:
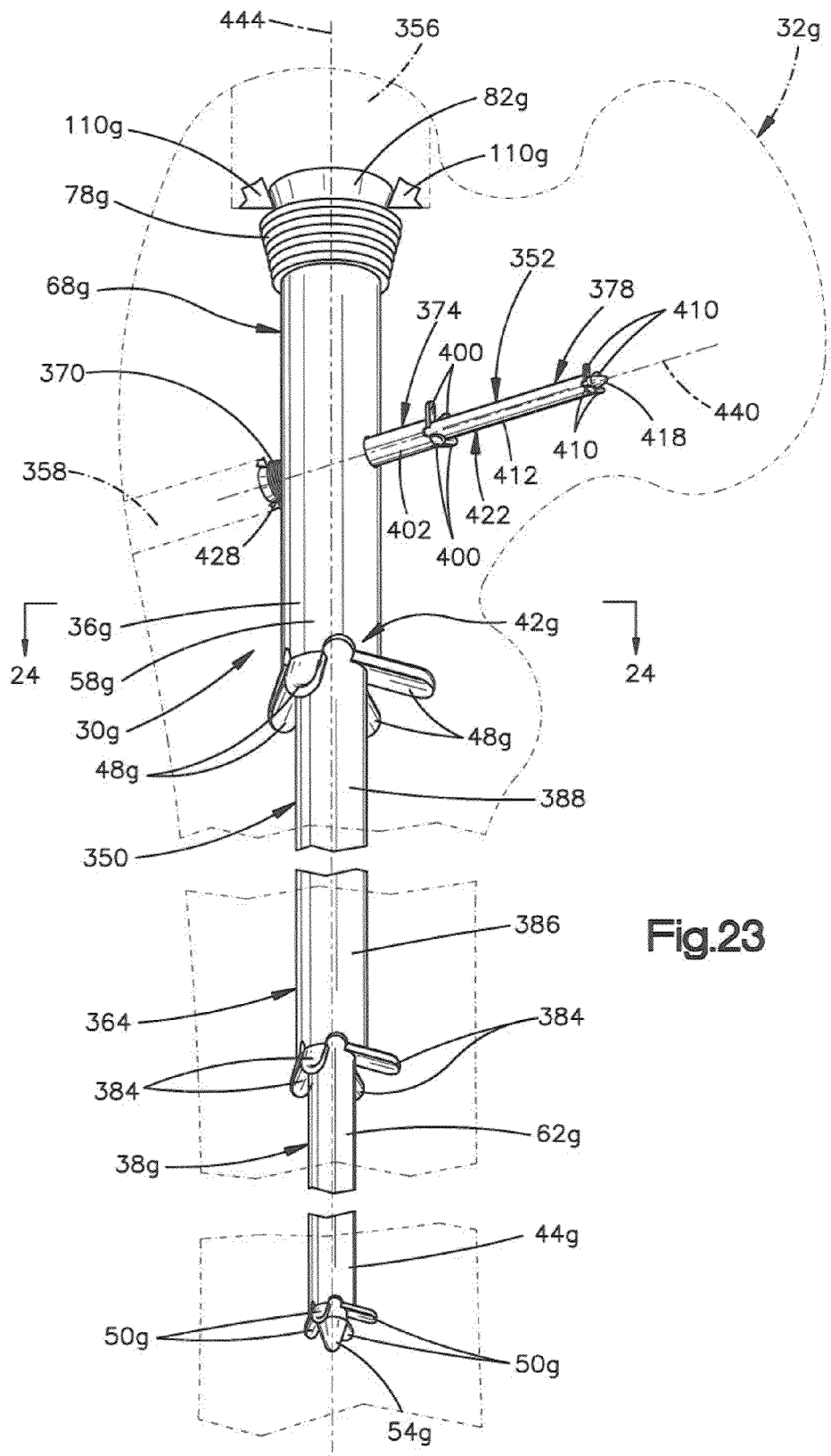
FIG. 23 is a fragmentary schematic illustration depicting the manner in which a fastener assembly, having main and secondary fastener assemblies with a construction generally similar to the fastener apparatus of FIGS. 1-13, may be positioned in a bone or other tissue in a patient's body.

The fastener assembly or apparatus 30 of FIG. 1 has an external thread convolution 78 on the proximal end portion 68 of the fastener assembly or apparatus to engage an article to be implanted in a patient's body or to engage either hard or soft tissue in a patient's body. In the embodiment of the invention illustrated in FIG. 9, a fastener assembly or apparatus 30a has a proximal end portion 68a which engages a patient's body tissue or an implant. In the embodiment of the invention illustrated in FIG. 23, a secondary fastener assembly extends through a proximal end portion of a main fastener assembly to anchor the main fastener assembly in a patient's body tissue. Since the embodiment of the invention illustrated in FIG. 23 is generally similar to the embodiments of the invention illustrated in FIGS. 1-13, similar numerals will be used to designate similar components, the suffix letter "g" being associated with the numerals of FIG. 23 to avoid confusion.

A fastener assembly or apparatus 30g includes a main fastener assembly 350 and a secondary fastener assembly 352. The secondary fastener assembly 352 extends through the main fastener assembly 350 and anchors a proximal end portion 68g of the main fastener assembly in a patient's body tissue 32g. In the illustration of FIG. 23, the fastener assembly or apparatus 30g is shown in association with the femur bone in a patient's body. However, it should be understood that the body tissue 32g may be a bone other then the femur bone or may be soft tissue.

The main fastener assembly 350 extends into an opening 356 formed in the body tissue 32g. The secondary fastener assembly 352 extends into an opening 358 formed in the body tissue 32g. The opening 358 has a central axis which extends transversely to a central axis of the opening 356. The central axis of the opening 358 intersects the central axis of the opening 356. The central axis of the opening 358 is skewed at an acute angle relative to the central axis of the opening 356. However, if desired, the central axis of the opening 358 may extend perpendicular to the central axis of the opening 356 and/or may be offset to one side of the central axis of the opening 356.

The main fastener assembly 350 has the same general construction as the fastener assembly or apparatus 30 of FIG. 1. The main fastener assembly 350 includes an outer fastener assembly 36g and an inner fastener assembly 38g. In addition, the main fastener assembly 350 includes an intermediate fastener assembly 364. Although the illustrated main fastener assembly 350 includes three interconnected fastener assemblies, that is, the outer fastener assembly 36g, the inner fastener assembly 38g, and the intermediate fastener assembly 364, the main fastener assembly may include either a greater or lesser number of interconnected fastener assemblies.

The secondary fastener assembly 352 has the same general construction as the fastener assembly or apparatus 30 of FIG. 1. The secondary fastener assembly 352 includes a proximal end portion 370 having the same construction as the proximal end portion 68 of the fastener assembly or apparatus 30 of FIG. 1. In addition, the secondary fastener assembly 352 includes an outer fastener assembly 374 having the same construction as the outer fastener assembly 36 of FIG. 1. The secondary fastener assembly 352 includes an inner fastener assembly 378 having the same construction as the inner fastener assembly 38 of FIG. 1. Although the secondary fastener assembly 352 includes two interconnected fastener assemblies, that is, the outer fastener assembly 374 and the inner fastener assembly 378, the secondary fastener assembly 352 may include either a greater or lesser number of fastener assemblies. For example, the secondary fastener assembly 352 may include an intermediate fastener assembly having the same construction as the intermediate fastener assembly 364.

When the main fastener assembly 350 is in the extended condition of FIG. 23, arm sections 48g on a distal end portion 42g of the outer fastener assembly 36g extend radially outward in a circular array and engage the body tissue 32g to hold the fastener assembly or apparatus 30g against movement relative to the body tissue. When the main fastener assembly 350 is in the extended condition of FIG. 23, arm sections 50g on a distal end portion 44g of the inner fastener assembly 38g extend radially outward in a circular array and engage the body tissue 32g to hold the fastener assembly or apparatus 30g against movement relative to the body tissue. Similarly, when the main fastener assembly 350 is in the extended condition of FIG. 23, arm sections 384 on a distal end portion 386 of the intermediate fastener assembly 364 extend radially outward in a circular array and engage the body tissue 32g to hold the fastener assembly or apparatus 30g against movement relative to the body tissue 32g.

The arm sections 48g on the distal end portion 42g of the outer fastener assembly 36g engage the intermediate fastener assembly 364 to hold the arm sections 48g in the radially outwardly projecting positions illustrated in FIG. 23. Similarly, the arm sections 384 on the distal end portion 386 of the intermediate fastener assembly 364 engage the inner fastener assembly 38g to hold the arm sections 384 in the radially outwardly projecting positions illustrated in FIG. 23. A retainer member 54g is disposed in the inner fastener assembly 38g and is engaged by the arm sections 50g on the distal end portion 44g of the inner fastener assembly. Engagement of the arm sections 50g with the retainer member 54g holds the arm sections 50g in the radially outwardly projecting positions illustrated in FIG. 23.

In the embodiment of the invention illustrated in FIGS. 1-8, the retainer member 54 (FIG. 8) extends throughout substantially the entire length of the inner fastener assembly 38. The retainer member 54 (FIG. 8) is provided with an external thread convolution 160 (FIG. 8) which engages an internal thread convolution 164 (FIG. 3) on the inner sleeve 62 at the proximal end portion of the inner sleeve 62. In the embodiment of the invention illustrated in FIG. 23, the retainer member 54g has a shorter axial extent than the retainer member 54 of FIG. 8. The retainer member 54g (FIG. 23) has an external thread convolution which engages an internal thread convolution formed on the inside of an inner sleeve 62g of the inner fastener assembly 38g at a location approximately midway between axially opposite ends of the inner sleeve 62g. Therefore, the proximal end of the retainer member 54g is disposed axially downward (as viewed in FIG. 23) from the secondary fastener assembly 352. This enables the secondary fastener assembly 352 to extend through the main fastener assembly 350 at a location above (as viewed in FIG. 23) the proximal end of the retainer member 54g.

The secondary fastener assembly 352 has the same construction as the fastener assembly or apparatus 30 of FIG. 1. When the secondary fastener assembly 352 is in the extended condition of FIG. 23, arm sections 400 on a distal end portion 402 of the outer fastener assembly 374 extend radially outward in a circular array and engage the body tissue 32g to hold secondary fastener assembly 352 against movement relative to the body tissue. Similarly, when the secondary fastener assembly 352 is in the extended condition of FIG. 23, arm sections 410 on the distal end portion 412 of the inner fastener assembly 378 extend radially outward in a circular array and engage the body tissue 32g to hold the secondary fastener assembly 352 against movement relative to the body tissue.

The arm sections 400 on the distal end portion 402 of the outer fastener assembly 374 engage the inner fastener assembly 378 to hold the arm sections 400 in the radially outwardly projecting extending projections illustrated in FIG. 23. A retainer member 418 is disposed in the inner fastener assembly 378 and is engaged by the arm sections 410 on the distal end portion 412 of the inner fastener assembly 378. Engagement of the arm sections 410 with the retainer member 418 holds the arm sections in their radially outwardly extended positions illustrated in FIG. 23. The retainer member 418 has the same construction as the retainer member 54 of FIG. 8. Thus, the retainer member 418 has an external thread convolution, corresponding to the external thread convolution 160 of FIG. 8, which engages an internal thread convolution, corresponding to the internal thread convolution 164 of FIG. 3, on an inner sleeve 422 of the inner fastener assembly 378.

The proximal end portion 370 of the outer fastener assembly 374 (FIG. 23) engages the outer fastener assembly 36g of the main fastener assembly 350. If desired, the proximal end portion 68g of the outer fastener assembly 36g (FIG. 23) may be provided with an internal thread convolution which engages an external thread convolution 428 on the proximal end portion 370 of the outer fastener assembly 374 of the secondary fastener assembly 352 to interconnect the main fastener assembly 350 and secondary fastener assembly 352. Of course, the main fastener assembly 350 and secondary fastener assembly 352 may be interconnected in a different manner if desired. For example, the thread convolution 428 may be omitted.

The fastener assemblies 36g, 350, 38g, 374 and 378 (FIG. 23) all have distal end portions with the same construction as the distal end portion 42 (FIGS. 2 and 7) of the sleeve 58. Thus, the distal end portions of the fastener assemblies 36g, 350, 38g, 374 and 378 (FIG. 23) all have a plurality of arm sections which are formed by a plurality of slots, corresponding to the slots 86 of FIG. 7. As was previously described in connection with the embodiment of FIGS. 1-7, each of the slots has parallel side surfaces, corresponding to the side surfaces 89 and 90 (FIGS. 2 and 7). Each of the slots in the distal end portions of the sleeves of the fastener assemblies of FIG. 23 have circular openings, corresponding to the circular opening 88 of FIG. 7, at the ends of the slots. The circular openings at the ends of the slots in the distal end portions of the fastener assemblies of FIG. 23 have a diameter which is greater than the distance between parallel side surfaces of associated slots.

When the fastener assembly or apparatus 30g (FIG. 23) is to be installed in body tissue 32g, the main fastener assembly 350 is moved into the body tissue 32g. The main fastener assembly 350 is then operated from a retracted condition to the extended condition of FIG. 23. The secondary fastener assembly 352 is then moved through an opening formed in the main fastener assembly 350. The secondary fastener assembly 352 is operated from a retracted condition to an extended condition to install the secondary fastener assembly 352 in the body tissue 32g.

When the main fastener assembly 350 is to be installed in body tissue 32g (FIG. 23), the outer fastener assembly 36g is positioned in the body tissue with an outer sleeve 58g in the retracted condition. The outer sleeve 58g is then operated to the extended condition to FIG. 23. The outer fastener assembly 38g may be operated to the extended condition either before or during telescopic insertion of the intermediate fastener assembly 364 into the outer fastener assembly 36g. If the outer fastener assembly 36g is to be operated to the extended condition before insertion of the intermediate fastener assembly, an actuator member, corresponding to the actuator member 112 of FIG. 5 is utilized. If the outer fastener assembly 36g is to be operated to the extended condition during insertion of the intermediate fastener assembly 364, force is transmitted from the retracted intermediate fastener assembly 364 to the outer fastener assembly 36g to extend the outer fastener assembly.

When the intermediate fastener assembly 364 is to be installed in body tissue 32g, the intermediate fastener assembly 364 is telescopically inserted into the outer fastener assembly 36g with a sleeve of the intermediate fastener assembly 364 in the retracted condition. The intermediate fastener assembly 364 may be operated from the retracted condition to the extended condition illustrated in FIG. 23 either before the inner fastener assembly 38g is telescopically inserted into the intermediate fastener assembly 364 or simultaneously with insertion of the inner fastener assembly 38g into the intermediate fastener assembly 364.

When the inner fastener assembly 38g is to be installed in the body tissue 32g, the inner fastener assembly is telescopically inserted into the intermediate fastener assembly 364 with the inner sleeve 62g of the inner fastener assembly in the retracted condition. The inner fastener assembly 38g is then operated from the retracted condition to the extended condition of FIG. 23.

The outer sleeve 58g of the outer fastener assembly 36g is inserted into the body tissue 32g with a retracted distal end portion 42g leading. As the outer sleeve 58g is moved into the body tissue 32g, an external thread convolution 78g is moved into engagement with the body tissue. A tool is then utilized to engage wrenching flats corresponding to the wrenching flats 84 of FIG. 2, to rotate the outer sleeve 58g (FIG. 23) relative to the body tissue 32g and cause the external thread convolution 78g to form internal threads in the body tissue.

When the outer sleeve 58g of the outer fastener assembly 36g has been moved into the desired position relative to the body tissue 32g, the distal end portion of the outer sleeve 58g is extended. To extend the distal end portion 42g of the outer sleeve 58g, a projecting end portion 82g of the outer sleeve 58g is engaged by a gripper 110g. While the projecting end portion 82g of the outer sleeve 58 is engaged by the gripper 110g, a cylindrical actuator member, corresponding to the actuator member 112 of FIG. 5, may be moved into the cylindrical central opening in the outer sleeve 58g. The actuator member is telescopically inserted into the outer sleeve 58g with a conical nose portion of the actuator member leading.

The nose end portion of the actuator member moves into engagement with sloping side or cam surfaces, corresponding to the cam surfaces of 124 of FIG. 7, on the arm sections 48g of the outer sleeve 58g. At the same time, the gripper 110g is pulling the end portion 82g of the outer sleeve 58g upward (as viewed in FIG. 23). As the outer sleeve 58g is operated from the retracted condition to the extended condition, the tissue 32g is deflected by the arm sections 48g. The distal arm sections 48g and proximal end portion 68g of the outer sleeve 58g engage the body tissue 32g to block axial movement of the outer sleeve relative to the body tissue.

Once the arm sections 48g on the outer sleeve 58g have moved to the extended condition of FIG. 23 by the application of force against the distal end portion 42g by an actuator member, corresponding to the actuator member 112 of FIG. 5, the actuator member is withdrawn from the outer sleeve 58g. The gripper 110g (FIG. 23) maintains a secured grip on the projecting end portion 82g of the outer sleeve 58g as the actuator member is withdrawn from the outer sleeve. The retracted intermediate fastener assembly 364 is then telescopically inserted into the extended outer sleeve 58g. If desired, the retracted intermediate fastener assembly 364 may be used to extend the retracted outer sleeve 58g of the outer fastener assembly 36g.

The retracted distal end portion 386 of the intermediate fastener assembly 364 is moved axially past the extended arm sections 48g on the outer sleeve 58g and into engagement with the body tissue 32g. The intermediate fastener assembly 364 then continues to move further into the body tissue 32g to the position illustrated in FIG. 23 while the intermediate fastener assembly remains in the retracted condition. As the intermediate fastener assembly 364 moves past the extended distal end portion 42g of the outer fastener assembly 36g, the retracted leading distal end portion 386 of the intermediate fastener assembly 364 displaces body tissue 32g. If desired, an opening may be formed in the body tissue 32g to receive the retracted distal end portion 386 of the intermediate fastener assembly 364.

As the intermediate fastener assembly 364 moves into the outer fastener assembly 36g, a thread convolution, corresponding to the thread convolution 92 of FIG. 4, on the outside of the intermediate fastener assembly 364 engages an internal thread convolution, corresponding to the thread convolution 93 of FIG. 4, formed within the hollow proximal end portion 68g of the outer fastener assembly 36g. The intermediate fastener assembly 364 may then be rotated to cause the external thread convolution on the intermediate fastener assembly to engage the internal thread convolution in the proximal end portion 68g of the outer fastener assembly 36g.

The internal thread convolution in the outer fastener assembly 36g may be disposed downward (as viewed in FIG. 23) from a location where the secondary fastener assembly 352 extends through the main fastener assembly 350. This would result in a cylindrical sleeve 388 of the intermediate fastener assembly 364 being offset downward (as viewed in FIG. 23) from the secondary fastener assembly 352. Of course, the proximal end portion of the intermediate fastener assembly 364 may be aligned with the proximal end portion of the outer fastener assembly 36g. If this is done, the secondary fastener assembly 352 will extend through both the outer fastener assembly 36g and the intermediate fastener assembly 364. If desired, the external thread convolution on the intermediate fastener assembly 364 may be omitted and the intermediate fastener assembly provided with a smooth arcuate surface which engages a similarly shaped smooth arcuate surface formed within the outer fastener assembly 36g.

During axial movement of the intermediate fastener assembly 364 (FIG. 23) into the outer fastener assembly 36g, the gripper 110g is effective to hold the outer fastener assembly 36g against axial movement relative to the body tissue 32g. The gripper 110g is effective to hold the outer fastener assembly 36g against both axial and/or rotational movement relative to the body tissue 32g during axial and/or rotational movement of the intermediate fastener assembly 364 relative to the outer fastener assembly 36g to tightly interconnect the thread convolutions on the intermediate fastener assembly 364 and outer fastener assembly 36g.

When the retracted intermediate fastener assembly 364 has been telescopically inserted into the extended outer fastener assembly 36g and moved to a desired position relative to the body tissue 32g, cam surfaces on arm sections 48g in the distal end portion 42g of the outer fastener assembly 36g engage a cylindrical outer side surface on the sleeve 388 of the intermediate fastener assembly 364. Engagement of the arm sections 48g with the outer side surface of the intermediate fastener assembly 364 holds the arm sections 48g in the extended condition illustrated in FIG. 23. Thus, the intermediate fastener assembly 364 locks the arm sections 48g in the extended or expanded condition.

The intermediate fastener assembly 364 is operated from a retracted condition to the extended condition of FIG. 23 using an actuator member, corresponding to the actuator member 112 of FIG. 5, in the manner previously described. Rather than using an actuator member to extend the retracted distal end portion 386 of the intermediate fastener assembly 364, the retracted inner fastener assembly 38g may be utilized to extend the intermediate fastener assembly 364g. When this is to be done, the retracted inner fastener assembly 38g is telescopically inserted into the retracted intermediate fastener assembly 364. While the gripper 110g pulls on the proximal end portion of the intermediate fastener assembly 364, the retracted distal end portion 44g of the inner fastener assembly 38g is pressed against cam surfaces on the arm sections 384 of the intermediate fastener assembly 364. The force applied against the cam surfaces, corresponding to the cam surfaces 124 of FIG. 7, by the retracted inner fastener assembly 38g pivots the arm sections 384 radially outward and moves the body tissue 32g.

Once the intermediate fastener assembly 364 has been expanded, the retracted inner fastener assembly 38g is telescopically inserted into the extended intermediate fastener assembly 364. As the inner fastener assembly 38g is inserted into the intermediate fastener assembly 364, the leading distal end portion 44g of the inner fastener assembly 38g moves past the extended arm sections 384 on the intermediate fastener assembly 364 and into engagement with the body tissue 32g. The inner fastener assembly 38g continues to move further into the body tissue 32g to the position illustrated in FIG. 23 while the inner fastener assembly remains in the contracted or retracted condition. As the inner fastener assembly 38g moves past the extended distal end portion 386 of the intermediate fastener assembly 364, a retracted leading distal end portion 44g of the inner fastener assembly 38g displaces body tissue 32g. If desired, an opening may be formed in the body tissue 32g to receive the retracted inner fastener assembly 38g.

As the inner fastener assembly 38g moves into the intermediate fastener assembly 364, the inner fastener assembly 38g is rotated to cause an external thread convolution, corresponding to the external thread convolution 92 of FIGS. 3 and 4, on the outside of the inner fastener assembly 38g to engage an internal thread convolution, corresponding to the internal thread convolution 93 of FIG. 4, in the proximal end portion of the intermediate fastener assembly 364 to interconnect the inner fastener assembly 38g and the intermediate fastener assembly 364.

The internal thread convolution on the intermediate fastener assembly 364 may be disposed downward (as viewed in FIG. 23) from a location where the secondary fastener assembly 352 extends through the main fastener assembly 350. This would result in the inner fastener assembly 38g being offset downward (as viewed in FIG. 23) from the secondary fastener assembly 352. Of course, the proximal end portion of the inner fastener assembly 38g may be aligned with the proximal end portion of the outer fastener assembly 36g. If this is done, the secondary fastener assembly 352 will extend through the inner fastener assembly 38g and the outer fastener assembly 36g. If desired, the external thread convolution on the inner fastener assembly 38g may be omitted and the inner fastener assembly provided with a smooth arcuate surface which engages a similarly shaped smooth arcuate surface formed within the proximal end portion of the intermediate fastener assembly 364.

During axial movement of the inner fastener assembly 38g into the intermediate fastener assembly 364 and into the outer fastener assembly 36g, the gripper 110g holds the outer fastener assembly 36g and intermediate fastener assembly 364 against axial movement relative to the body tissue 32g. The gripper 110g is effective to hold the outer fastener assembly 36g against axial and/or rotational movement relative to the body tissue 32g during axial and/or rotational movement of the inner fastener assembly 38g relative to both the outer fastener assembly 36g and the intermediate fastener assembly 364 to tightly interconnect the thread convolution on the outside of the inner fastener assembly 38g with the thread convolution formed on the inside of the intermediate fastener assembly 364.

When the retracted inner fastener assembly 38g has been telescopically inserted into the expanded intermediate fastener section 364 and moved to the desired position relative to the body tissue 32g, cam surfaces, corresponding to the cam surfaces 124 of FIG. 7, on the arm sections 384 in the distal end portion 386 of the intermediate fastener assembly 364 engage a cylindrical outer side surface on the inner sleeve 62g of the inner fastener assembly 38g. Engagement of the arm sections 384 with the outer side surface of the inner sleeve 62g holds the arm sections 384 in the expanded or extended condition illustrated in FIG. 23. Thus, the inner sleeve 62g locks the arm sections 384 in the extended or expanded condition.

Once the contracted inner fastener assembly 38g has been positioned relative to the intermediate fastener assembly 364 and body tissue 32g, the retracted inner fastener assembly 38g is operated from the retracted condition to the extended condition. To operate the inner sleeve 62g to the extended condition, a cylindrical actuator member, corresponding to the actuator member 144 of FIG. 6, is telescopically inserted into a cylindrical opening into the inner sleeve 62g of the inner fastener assembly 38g. Insertion of the actuator member into the inner sleeve 62g of the inner fastener assembly 38g results in a conical nose end portion on the actuator member moving into engagement with cam surfaces, corresponding to the cam surfaces 124 of FIG. 7, at the distal end portion 44g of the retracted inner fastener assembly 38g.

Once the actuator member has engaged the cam surfaces on the arm sections 50g at the distal end portion 44g of the retracted inner fastener assembly 38g, force is applied against a proximal end portion of the actuator member. At the same time, the gripper 110g engages the projecting end portion 82g on the proximal end portion 68g of the outer fastener assembly 36g. The gripper 110g pulls the outer fastener assembly 36g upward (as viewed in FIG. 23) while the actuator member presses downward against the distal end portion of the retracted inner fastener assembly 38g.

The force applied against the proximal end portion of the actuator member is directed downward (as viewed in FIG. 23). This force is applied to cam surfaces on the arm sections 50g of the inner fastener assembly 38g. The force is transmitted from the distal end portion of the inner sleeve 62g to thread convolutions, corresponding to the thread convolutions 92 and 93 of FIG. 4, interconnecting the proximal end portions of the inner fastener assembly 38g and intermediate fastener assembly 364. This force is transmitted through thread convolutions interconnecting the proximal end portions of the intermediate fastener assembly 364 and the outer fastener assembly 36g. The gripper 110g holds the proximal end portions 68g of the outer fastener assembly 36g against movement relative to the body tissue 32g.

The force applied to the actuator member to expand the inner fastener assembly 38g is in an opposite direction to the force applied to the gripper 110g. Therefore, the two forces tend to cancel each other.

When the arm sections 50g of the inner fastener assembly 38g have been moved to their fully expanded or extended conditions (FIG. 23), the actuator member, corresponding to the actuator member 144 of FIG. 6, is withdrawn from the central opening in the inner sleeve 62g. Once the actuator member has been withdrawn from the inner sleeve 62g, a retainer member 54g, corresponding to the retainer member 54 of FIG. 8, is moved into the inner sleeve 62g to a location where an external thread convolution on the proximal end portion of the retainer member engages an internal thread convolution on the inner sleeve 62g. The internal thread convolution on the inner sleeve 62g, that is, the thread convolution which is engaged by the external thread convolution on the retainer member 54g, is at a location below (as viewed in FIG. 23) the secondary fastener assembly 352.

A suitable tool engages wrenching flats formed in the proximal end portion of the retainer member 54g. The tool rotates the retainer member 54g to tightly engage the thread convolution on the retainer member 54g with the thread convolution on the inner sleeve 62g. The inner sleeve 62g, intermediate fastener assembly 364 and outer fastener assembly 36g are held against rotation relative to the body tissue 32g by the gripper 110g as the retainer is rotated relative to the inner sleeve 62g.

A nose end portion, corresponding to the nose end portion 166 of FIG. 8, on the retainer member 54g extends outward past cam surfaces on the arm sections 50g and the distal end portion 44g of the inner sleeve 62g. The arm sections 50g on the distal end portions 44g of the inner sleeve 62g engage a cylindrical side surface on the retainer member 54g. This results in the arm sections being held in the extended condition of FIG. 23 by engagement with the retainer member 64g.

Once the main fastener assembly 350 has been mounted in the body tissue 32g in the manner previously explained, the secondary fastener 352 is moved through the main fastener assembly 350 and mounted in the body tissue 32g. When the main fastener assembly 350 is mounted in the body tissue 32g, openings in the outer fastener assembly 36g, intermediate fastener assembly 364 and inner fastener assembly 38g are aligned so that the retracted secondary fastener assembly 352 can be positioned in the openings in the manner illustrated in FIG. 23. When the secondary fastener assembly 352 is positioned in the openings in the main fastener assembly 350, in the manner illustrated in FIG. 23, a central axis 440 of the secondary fastener assembly 352 intersects a central axis 444 of the main fastener assembly 350.

As was previously mentioned herein, the proximal end portions of the intermediate fastener assembly 364 and inner fastener assembly 38g may be disposed below (as viewed in FIG. 23) the location where the secondary fastener assembly 352 extends through the main fastener assembly 350. If this arrangement is selected, the secondary fastener assembly 352 would extend through only the outer fastener assembly 36g of the main fastener assembly 350. Of course, the proximal end portions of the intermediate fastener assembly 364 and inner fastener assembly 38g may be adjacent the proximal end portion of the outer fastener assembly 36g. If this arrangement is selected, the secondary fastener assembly 352 would extend through the outer fastener assembly 36g, intermediate fastener assembly 364, and inner fastener assembly 38g.

The central axis 440 of the secondary fastener assembly 352 is skewed at an acute angle relative to the central axis 444 of the main fastener assembly 350. However, the central axis 440 of the secondary fastener assembly 352 may extend perpendicular to the central axis 444 of the main fastener assembly if desired. In the illustrated embodiment of the invention, the central axis 440 of the secondary fastener assembly extends through, the central axis 444 of the main fastener assembly 350. However, if desired, the central axis 440 of the secondary fastener assembly may be offset to one side of the central axis 444 of the main fastener assembly 350.

The secondary fastener assembly 352 has the same construction and is installed in the same manner as previously described in conjunction with the embodiment of the invention illustrated in FIGS. 1-8. Thus, the outer fastener assembly 374 can be moved through openings in the main fastener assembly 350 and operated to the extended condition in the manner illustrated schematically in FIG. 23. The inner fastener assembly 378 will then be inserted into the outer fastener assembly 374 and extended. A retainer member 418 may be utilized to retain the inner fastener assembly 378 in its extended condition.

The openings in the various cylindrical sleeves which are disposed in a telescopic relationship with each and form part of the main fastener assembly 350 are aligned with each other during installation of the main fastener assembly 350 in the body tissue 32g. However, the openings through which the secondary fastener assembly 352 is to extend may be absent from the main fastener assembly 350 when the main fastener assembly is being installed in the body tissue 32g. Once the main fastener assembly 350 has been installed in the body tissue 350, the openings for receiving the secondary fastener assembly 352 may be formed in the main fastener assembly 350. This may be done by drilling diametrically through the main fastener assembly 350 after the main fastener assembly has been installed in the body tissue 32g.

To facilitate drilling of the main fastener assembly 350, an annular array of small recesses may be provided around the proximal end portion 68g of the outer sleeve 58g of the outer fastener assembly 36g. These small recesses or indentations would facilitate positioning of the drill in a desired orientation relative to the main fastener assembly 350 after the main fastener assembly has been installed in the body tissue 32g. Alternatively, aligned openings may be formed through the outer sleeve 58g of the outer fastener assembly 36g. These openings would be positioned in a desired orientation relative to the body tissue 32g during installation of the main fastener assembly 350. The intermediate fastener assembly 364 and inner fastener assembly 38g would be free of openings to receive the secondary fastener assembly 352. The opening formed in the outer sleeve 58g of the outer fastener assembly 36g would be engaged by a drill or other cutting tool to position the drill or other cutting tool relative to the main fastener assembly 350. The drill or cutting tool would then be utilized to form the openings in the intermediate fastener assembly 364 and inner fastener assembly 38g through which the secondary fastener assembly 352 is subsequently installed.

It is contemplated that the outer fastener assembly 36g may be formed with openings which receive the secondary fastener and have one configuration while the intermediate fastener assembly 364 and/or inner fastener assembly 38g have openings with a different configuration. For example, circular openings may be formed in the outer fastener assembly 36g and openings having a generally U-shaped configuration may be provided in the intermediate fastener assembly 364 and/or inner fastener assembly 38g.

The main fastener assembly 350 and/or the secondary fastener assembly 352 (FIG. 23) may be modified to have an external thread convolution, corresponding to the thread convolution 180 (FIG. 9) and/or the thread convolution 200 (FIG. 10). If desired either or both of the thread convolutions may be mounted on a cylindrical tube, corresponding to the tube 194c of FIG. 11. The main fastener assembly 350 and/or the secondary fastener assembly 352 (FIG. 23) may be modified to have external ribs, corresponding to the ribs 210 (FIG. 12). If desired, the main fastener assembly 350 and/or the secondary fastener assembly 352 (FIG. 23) may be modified to have a porous outer side surface, corresponding to the porous outer surface 216 (FIG. 13), to promote tissue in-growth. The main fastener assembly 350 (FIG. 23) may be utilized in association implants similar to the implants of FIGS. 14-19. It should be understood that the main fastener assembly 350 and/or the secondary fastener assembly 352 may include any of the features illustrated in or described in connection with FIGS. 1 through 22 of the drawings.

In order to maintain the openings in the outer fastener assembly 36g, intermediate fastener assembly 364 and inner fastener assembly 38g in alignment with each other to facilitate insertion of the secondary fastener assembly 352, index surfaces 460 (FIG. 24) may be formed in the fastener assemblies. To form the index surfaces 460, a radially inwardly extending index projection 464 may be formed on the inside of the outer sleeve 58g. The index projection 464 on the outer sleeve 58g engages a correspondingly shaped recess formed in the sleeve 388 of the intermediate fastener assembly 364. Similarly, an index projection 466 on the inside of the outer sleeve 388 of the intermediate fastener assembly 364 engages a similar shaped recess formed in the inner sleeve 62g of the inner fastener assembly 38g. An index projection 468 formed on the inner sleeve 62g engages a similarly shaped recess formed in the retainer member 54g.

The index projections and correspondingly shaped recesses extend throughout the axial extent of the sleeves 58g, 388 and 62g. However, the index projections and correspondingly shaped recesses may have a shorter axial extent if desired. The index projections and recesses have longitudinal central axes which extend parallel to the longitudinal central axis 444 (FIG. 23) of the main fastener assembly 350. The index projections 464-468 (FIG. 24) and the associated recesses cooperate to maintain openings formed in the outer fastener assembly 36g, inner fastener assembly 38g and intermediate fastener assembly 364 in alignment with each other to facilitate insertion of the secondary fastener assembly 352 through the main fastener assembly 350.

In the embodiment of the invention illustrated in FIG. 24, the index projections 464-468 have been illustrated as having a generally V-shaped cross sectional configuration. It is contemplated that the index projections 464-468 may have a different cross sectional configuration if desired. For example, the index projections may have an arcuate cross sectional configuration.

Alternative Secondary
Fastener Assembly

In the embodiment of the invention illustrated in FIG. 23, the secondary fastener assembly 352 is relatively thin, that is, it has a relatively small outside diameter. In the embodiment of the invention illustrated in FIG. 25, the secondary fastener assembly is thicker, that is, the secondary fastener assembly has a relatively large outside diameter. Since the embodiment of the invention illustrated in FIG. 25 is generally the same as the embodiments of the invention illustrated in FIGS. 1-24, similar numerals will be utilized to designate similar components. The suffix letter "h" being associated with the numerals of FIG. 25 to avoid confusion.

A fastener assembly or apparatus 30h includes a main fastener assembly 350h and a secondary fastener assembly 352h. The secondary fastener assembly 352h extends through the main fastener assembly 350h and anchors a proximal end portion 68h of the main fastener assembly in a patient's body tissue 32h. In the illustration of FIG. 25, the fastener assembly or apparatus 30h is shown in association with the femur bone in a patient's body. However, it should be understood that the body tissue 32h may be a bone other than the femur bone or may be soft tissue. The main fastener assembly 350h extends into an opening 356h formed in the body tissue 32h. The secondary fastener assembly 352h extends into an opening 358h formed in the body tissue 32h. The opening 358h has a central axis which extends transversely to a central axis 444h of the opening 356h and the central axis of the main fastener assembly 350h. The central axis 440h intersects the central axis 444h.

The main fastener assembly 350h has the same general construction as the fastener assembly or apparatus 30 of FIG. 1. The main fastener assembly 350h includes an outer fastener assembly 36h and an inner fastener assembly 38h. In addition, the main fastener assembly 350h includes an intermediate fastener assembly 364h. Although the illustrated main fastener assembly 350h includes three interconnected fastener assemblies, that is, the outer fastener assembly 36h, the inner fastener assembly 38h and the intermediate fastener assembly 364h, the main fastener assembly may include a greater or lesser number of interconnected fastener assemblies.

The secondary fastener assembly 352h has the same general construction as the fastener assembly or apparatus 30 of FIG. 1. The secondary fastener assembly 352h includes an outer fastener assembly 374h having the same construction as the outer fastener assembly 36 of FIG. 1. The secondary fastener assembly 352h includes an inner fastener assembly 378h having the same construction as the inner fastener assembly 38 of FIG. 1. Although the secondary fastener assembly 352h includes two interconnected fastener assemblies, that is, the outer fastener assembly 374h and the inner fastener assembly 378h, the secondary fastener assembly 352h may include either a greater or lesser number of fastener assemblies.

In accordance with a feature of the embodiment of the invention illustrated in FIG. 25, the secondary fastener assembly 352h has a relatively large outside diameter. To enable the relatively thick secondary fastener assembly 352h to extend through the main fastener assembly 350h, in the manner illustrated schematically in FIG. 25, the intermediate fastener assembly 364h and inner fastener assembly 38h have proximal end portions which are disposed inside the outer sleeve 58h of the outer fastener assembly 36h. The intermediate fastener assembly 364h and inner fastener assembly 38h terminate below, that is, downwardly as viewed in FIG. 25, of the location where the secondary fastener assembly 352h extends through the main fastener assembly 350h. The intermediate fastener assembly 364h, inner fastener assembly 38h and retainer member 54h are secured against movement relative to each other and to the outer sleeve 58h of the outer fastener assembly 36h by a series of connections indicated schematically at 480 in FIG. 25. This results in the secondary fastener assembly 352h extending through only the outer sleeve 58h of the outer fastener assembly 36h. Therefore, the problem of aligning openings in the various fastener assemblies to receive the secondary fastener assembly 352h is eliminated.

In the embodiment of the invention illustrated in FIG. 25, the connections 480 are threaded connections. Thus, an internal thread convolution is formed on the inside of the outer sleeve 58h of the outer fastener assembly 36h. This internal thread convolution is engaged by an external thread convolution on the sleeve 388h of the intermediate fastener assembly 364h. Similarly, an internal thread convolution on the sleeve 388h is engaged by an external thread on the sleeve 62h of the inner fastener assembly 38h. Finally, an external thread convolution on the retainer member 54h engages an internal thread convolution on the sleeve 62h of the inner fastener assembly 38h. Although threaded connections have been illustrated schematically in FIG. 25, it should be understood that a different type of connection may be utilized to interconnect the outer fastener assembly 36h, intermediate fastener assembly 364h, intermediate fastener assembly 364h, inner fastener assembly 38h and retainer member 54h if desired.

The sleeves 388h and 62h and the retainer member 54h are interconnected with each other and with the outer sleeve 58h by rotating each of the sleeves 388h and 62h and the retainer member 54h about their coincident longitudinal central axes. Thus, the sleeve 388h is telescopically inserted into the outer sleeve 58h. The sleeve 388h is then engaged by a suitable tool and rotated about the axis 444h. This results in the internal thread on the outer sleeve 58h engaging the external thread on the sleeve 388h. The sleeve 62h and retainer member 54h are rotated in a similar manner. To rotate the sleeves, a tool such as a screw driver or Allen wrench (hex key) may be inserted into the outer sleeve 58h.

Conclusion

The present invention relates to a new and improved fastener apparatus 30 and a method of utilizing the fastener apparatus in association with a patient's body tissue 32. A fastener apparatus 30 constructed in accordance with the present invention may be used in anyone of many different ways with body tissue. For example, a fastener apparatus 30 constructed in accordance with the present invention may be used with body tissue in any of the ways previously mentioned herein. Of course, the fastener apparatus 30 may be used with body tissue in ways which have not been previously mentioned herein.

In one embodiment of the method and/or apparatus of the invention, the fastener apparatus 30 includes a fastener assembly 36 having a first sleeve 58 which is moved into a patient's body tissue. A distal end portion 42 of the first sleeve is extended in the patient's body tissue 32. At least a portion of a second sleeve 62 is moved through the first sleeve 58. A distal end portion 44 of the second sleeve 62 is extended in the patient's body tissue. During extension of the first sleeve 58 and/or the second sleeve 62, a proximal end portion 68 of the first sleeve may be gripped and pulled.

In another embodiment of the method and/or apparatus of the invention, a first sleeve 58a is rotated as it is moved into the patient's body tissue 32. As the first sleeve is rotated, a thread convolution 180 connected with the first sleeve engages the patient's body tissue. At least a portion of a second sleeve 62a is moved axially through the first sleeve 58a. A distal end portion 44a of the second sleeve 62a is extended in the patient's body tissue.

In another embodiment of the method and/or apparatus of the invention, a first sleeve 58b is moved into a patient's body tissue 32 and a distal end portion 42b of the first sleeve is extended. At least a portion of a second sleeve is moved through the first sleeve into the patient's body tissue. As the second sleeve 62b is moved into the patient's body tissue, the second sleeve is rotated about its longitudinal central axis to engage the patient's body tissue with a thread convolution 190b connected with the second sleeve.

In another embodiment of the method and/or apparatus of the invention, a first fastener assembly 350 is moved into a patient's body tissue with a distal end portion leading. A second fastener assembly 352 is moved into the patient's body tissue with a distal end portion leading. The distal end portion of the second fastener assembly 352 is moved through a portion of the first fastener assembly 350. The distal end portions of the first and/or second fastener assemblies are extended in the patient's body tissue.

A fastener apparatus constructed and/or used in accordance with the present invention may have only a single sleeve which is moved into a patient's body tissue. An actuator member 112 is moved into a central opening 116 in the sleeve and pressed against a distal end portion of the sleeve to expand the sleeve 58. A proximal end portion of the sleeve 58 is gripped and pulled during pressing of the actuator 112 member against the distal end portion of the sleeve. A retainer member 54 may be moved into the sleeve.

In another embodiment of the invention, a first or main fastener assembly 350 is moved into the patient's body tissue 32g. A distal end portion of the first or main fastener assembly 350 is extended at a plurality of locations 48g, 384, and 50g along a longitudinal axis 444 of the first or main fastener assembly. A second fastener assembly 352 is moved into the patient's body tissue 32g. The distal end portion of the second fastener assembly 352 is moved through the proximal end portion of the first fastener assembly. The distal end portion of the second fastener assembly 352 is extended in the patient's body tissue.

It should be understood that the method and apparatus of the present invention have a plurality of features. These features may be utilized together in the manner disclosed herein. Alternatively, the features may be utilized separately or in different combinations with each other or in combination with one or more features from the prior art. For example, an embodiment of the apparatus may include only a single sleeve or may include two or more sleeves. As another example, a fastener apparatus constructed in accordance with the present invention may be used in association with an implant having any one of many different constructions.

Having described the invention, the following is claimed:

1. A method of connecting a fastener apparatus with a patient's body tissue, said method comprising the steps of moving a first fastener assembly into a patient's body tissue with a distal end portion of the first fastener assembly leading, moving a second fastener assembly into a patient's body tissue with a distal end portion of the second fastener assembly leading, said step of moving a second fastener assembly into the patient's body tissue includes moving the distal end portion of the second fastener assembly through a portion of the first fastener assembly, extending the distal end portion of the first fastener assembly in the patient's body tissue, and extending the distal end portion of the second fastener assembly in the patient's body tissue while second fastener assembly extends through the first fastener assembly, said step of moving a first fastener assembly into a patient's body tissue includes moving a first sleeve into the patient's body tissue with a distal end portion of the first sleeve leading and moving at least a portion of a second sleeve axially through the first sleeve with a distal end portion of the second sleeve leading, said step of extending the distal end portion of the first fastener assembly in the patient's body tissue includes extending the distal end portion of the first sleeve in the patient's body tissue and extending the distal end portion of the second sleeve in the patient's body tissue, said step of moving a second fastener assembly into a patient's body tissue includes moving a third sleeve into the patient's body tissue with a distal end portion of the third sleeve leading, said step of moving a third sleeve into the patient's body tissue includes moving the distal end portion of the third sleeve through the first sleeve along a path which extends transverse to longitudinal axes of the first and second sleeves and extends through the longitudinal axes of the first and second sleeves, said step of extending the distal end portion of the second fastener assembly in the patient's body tissue includes extending the distal end portion of the third sleeve in the patient's body tissue.

2. A method as set forth in claim 1 further including the step of connecting a proximal end portion of the second sleeve with a portion of the first sleeve prior to performing said step of extending the distal end portion of the second sleeve and prior to performing said step of moving the distal end portion of the third sleeve through the first sleeve.

3. A method as set forth in claim 2 wherein said step of connecting a proximal end portion of the second sleeve with a portion of the first sleeve includes rotating the second sleeve relative to the first sleeve about the longitudinal axis of the second sleeve.

4. A method as set forth in claim 1 wherein said step of extending the distal end portion of the second sleeve includes moving an actuator member into the second sleeve and applying force against the distal end portion of the second sleeve with the actuator member and withdrawing the actuator member from the second sleeve before moving a third sleeve into the patient's body tissue.

5. A method a set forth in claim 1 wherein said step of extending the distal end portion of the first sleeve in the patient's body tissue includes applying force against the distal end portion of the first sleeve with the distal end portion of the second sleeve.

6. A method as set forth in claim 1 wherein said step of extending the distal end portion of the third sleeve includes moving an actuator member into the third sleeve and applying force against the distal end portion of the third sleeve with the actuator member, said step of moving the actuator member into the third sleeve includes moving the actuator member along the path which extends transverse to the longitudinal axes of the first and second sleeves and extends through the longitudinal axes of the first and second sleeves.

7. A method as set forth in claim 1 wherein said step of extending the distal end portion of the second sleeve includes moving an actuator member into a central opening in the second sleeve, pressing an end portion of the actuator member against the distal end portion of the second sleeve, gripping the proximal end portion of one of the first and second sleeves with a gripper, pulling on the gripper while pressing on the distal end portion of the second sleeve with the actuator member, and thereafter, removing the actuator member from the central opening in the second sleeve.

8. A method as set forth in claim 1 further including the step of providing the first sleeve with a porous outer surface to promote growth of body tissue into the first sleeve.

9. A method as set forth in claim 8 further including the step of providing the third sleeve with a porous outer surface to promote growth of body tissue into the third sleeve.

10. A method of connecting a fastener apparatus with a patient's body tissue, said method comprising the steps of moving a first fastener assembly into a patient's body tissue with a distal end portion of the first fastener assembly leading, moving a second fastener assembly into a patient's body tissue with a distal end portion of the second fastener assembly leading, said step of moving a second fastener assembly into the patient's body tissue includes moving the distal end portion of the second fastener assembly through a portion of the first fastener assembly, extending the distal end portion of the first fastener assembly in the patient's body tissue, and extending the distal end portion of the second fastener assembly in the patient's body tissue while second fastener assembly extends through the first fastener assembly, said step of moving a first fastener assembly into a patient's body tissue includes moving a first sleeve into the patient's body tissue with a distal end portion of the first sleeve leading, moving at least a portion of a second sleeve axially through the first sleeve with a distal end portion of the second sleeve leading, and moving at least a portion of a third sleeve axially through the second sleeve with a distal end portion of the third sleeve leading, said step of moving a second fastener assembly into a patient's body tissue includes moving a fourth sleeve into the patient's body tissue with a distal end portion of the fourth sleeve leading and moving at least a portion of a fifth sleeve axially through the fourth sleeve with a distal end portion of the fifth sleeve leading, said step of extending the distal end portion of the first fastener assembly in the patient's body tissue includes extending the distal end portion of the first sleeve in the patient's body tissue, extending the distal end portion of the second sleeve in the patient's body tissue after performing said step of extending the distal end portion of the first sleeve, and extending the distal end portion of the third sleeve in the patient's body tissue after performing said step of extending the distal end portion of the second sleeve, said step of extending the distal end portion of the second fastener assembly in the patient's body tissue includes extending the distal end portion of the fourth sleeve in the patient's body tissue and extending the distal end portion of the fifth sleeve in the patient's body tissue after performing said step of extending the distal end portion of the fourth sleeve.

11. A method as set forth in claim 10 wherein said step of extending the distal end portion of the third sleeve includes moving an actuator member into the third sleeve and applying force against the distal end portion of the third sleeve with the actuator member, said step of extending the distal end portion of the fifth sleeve includes moving an actuator member into the fifth sleeve and applying force against the distal end portion of the fifth sleeve with the actuator member which is moved into the fifth sleeve.

12. A method as set forth in claim 10 wherein said step of extending the distal end portion of the first sleeve includes applying force against the distal end portion of the first sleeve with the distal end portion of the second sleeve, said step of extending the distal end portion of the second sleeve includes applying force against the distal end portion of the second sleeve with the distal end portion of the third sleeve, said step of extending the distal end portion of the fourth sleeve includes applying force against the distal end portion of the fourth sleeve with the distal end portion of the fifth sleeve.

13. A method as set forth in claim 10 wherein said step of extending the distal end portion of the third sleeve includes moving an actuator member into a central opening in the third sleeve, pressing a leading end portion of the actuator member against a plurality of arm sections at the distal end portion of the third sleeve, moving the arm sections of the third sleeve away from each other under the influence of force applied against the arm sections by the actuator member, and pulling on a proximal end portion of the third sleeve while pressing the actuator member against the plurality of arm sections.

14. A method as set forth in claim 13 wherein said step of extending the distal end portion of the fifth sleeve includes moving an actuator member into a central opening in the fifth sleeve, pressing a leading end portion of the actuator member which is moved into the fifth sleeve against a plurality of arm sections at the distal end portion of the fifth sleeve, moving the arm sections of the fifth sleeve away from each other under the influence applied against the arm sections by the actuator member which is moved into the fifth sleeve, and pulling on the fifth sleeve while pressing the actuator member which is moved into the fifth sleeve against the arm sections of the fifth sleeve.

15. A method as set forth in claim 10 further including the step of providing the first sleeve with a porous outer surface to promote growth of body tissue into the first sleeve.

16. A method as set forth in claim 15 further including the step of providing the fourth sleeve with a porous outer surface to promote growth of body tissue into the fourth sleeve.

* * * * *